US011830983B2

(12) United States Patent
Jones et al.

(10) Patent No.: US 11,830,983 B2
(45) Date of Patent: *Nov. 28, 2023

(54) NON-AQUEOUS FLUORIDE SALTS, SOLUTIONS, AND THEIR USES

(71) Applicants: CALIFORNIA INSTITUTE OF TECHNOLOGY, Pasadena, CA (US); HONDA MOTOR CO., LTD., Tokyo (JP)

(72) Inventors: Simon C. Jones, Whittier, CA (US); Victoria K. Davis, Santa Clarita, CA (US); Christopher M. Bates, Monrovia, CA (US); Nebojsa Momcilovic, Vienna, VA (US); Brett M. Savoie, Pasadena, CA (US); Michael A. Webb, Pasadena, CA (US); Thomas F. Miller, III, South Pasadena, CA (US); Robert H. Grubbs, South Pasadena, CA (US); Christopher Brooks, Dublin, OH (US); Kaoru Omichi, Columbus, OH (US)

(73) Assignees: California Institute of Technology, Pasadena, CA (US); Honda Motor Co., Ltd., Tokyo (JP)

( * ) Notice: Subject to any disclaimer, the term of this patent is extended or adjusted under 35 U.S.C. 154(b) by 381 days.

This patent is subject to a terminal disclaimer.

(21) Appl. No.: 17/217,428

(22) Filed: Mar. 30, 2021

(65) Prior Publication Data

US 2021/0218063 A1 Jul. 15, 2021

Related U.S. Application Data

(63) Continuation of application No. 16/897,771, filed on Jun. 10, 2020, now Pat. No. 11,069,921, which is a
(Continued)

(51) Int. Cl.
*H01M 10/0568* (2010.01)
*H01M 10/0525* (2010.01)
(Continued)

(52) U.S. Cl.
CPC ....... *H01M 10/0568* (2013.01); *C07C 209/68* (2013.01); *H01M 10/054* (2013.01);
(Continued)

(58) Field of Classification Search
None
See application file for complete search history.

(56) References Cited

U.S. PATENT DOCUMENTS

| 4,052,539 A | 10/1977 | Shropshire et al. |
| 4,510,256 A | 4/1985 | Zones |

(Continued)

FOREIGN PATENT DOCUMENTS

| CN | 1287695 | 3/2001 |
| CN | 1535944 | 10/2004 |

(Continued)

OTHER PUBLICATIONS

Abboud et al. (1991) "Critical Compilation of Scales of Solvent Parameters. Part I. Pure, Non-Hydrogen Bond Donor Solvents," Pure Appl. Chem, 71:645-718.
(Continued)

*Primary Examiner* — Robert S Carrico
(74) *Attorney, Agent, or Firm* — Leydig, Voit & Mayer, Ltd.

(57) ABSTRACT

Electrolyte solutions including at least one anhydrous fluoride salt and at least one non-aqueous solvent are presented. The fluoride salt includes an organic cation having a charge center (e.g., N, P, S, or O) that does not possess a carbon in the β-position or does not possess a carbon in the β-position having a bound hydrogen. This salt structure facilitates its
(Continued)

ability to be made anhydrous without decomposition. Example anhydrous fluoride salts include (2,2-dimethylpropyl)trimethylammonium fluoride and bis(2,2-dimethylpropyl)dimethylammonium fluoride. Combining these fluoride salts with at least one fluorine-containing non-aqueous solvent (e.g., bis(2,2-trifluoroethyl)ether; (BTFE)) promotes solubility of the salt within the non-aqueous solvents. The solvent may be a mixture of at least one non-aqueous, fluorine-containing solvent and at least one other non-aqueous, fluorine or non-fluorine containing solvent (e.g., BTFE and propionitrile or dimethoxyethane). The electrolyte solutions may be employed in electrochemical cells, such as batteries, fuel cells, electrolysis systems, and capacitors.

11 Claims, 20 Drawing Sheets

Related U.S. Application Data continuation of application No. 15/228,876, filed on Aug. 4, 2016, now Pat. No. 10,720,666.

(60) Provisional application No. 62/200,998, filed on Aug. 4, 2015.

(51) Int. Cl.
H01M 10/0569 (2010.01)
H01M 10/054 (2010.01)
C07C 209/68 (2006.01)

(52) U.S. Cl.
CPC ... *H01M 10/0525* (2013.01); *H01M 10/0569* (2013.01); *H01M 2300/0025* (2013.01)

(56) References Cited

U.S. PATENT DOCUMENTS

| | | | |
|---|---|---|---|
| 5,876,685 | A | 3/1999 | Krulik et al. |
| 6,306,540 | B1 | 10/2001 | Hiroi et al. |
| 6,852,446 | B2 | 2/2005 | Barbarich |
| 7,169,333 | B2 | 1/2007 | Dobler et al. |
| 7,255,966 | B2 | 8/2007 | Kim et al. |
| 7,744,851 | B2 | 6/2010 | Dimagno et al. |
| 8,168,831 | B2 | 5/2012 | Otsuki et al. |
| 8,178,237 | B2 | 5/2012 | Ugawa |
| 8,377,586 | B2 | 2/2013 | Yazami |
| 8,658,309 | B2 | 2/2014 | Yazami |
| 9,045,579 | B2 | 6/2015 | Xia et al. |
| 9,166,249 | B2 | 10/2015 | Darolles et al. |
| 9,331,360 | B2 | 5/2016 | Weiss et al. |
| 9,382,387 | B2 | 7/2016 | Xia et al. |
| 9,453,943 | B2 | 9/2016 | Miyake et al. |
| 10,720,666 | B2 | 7/2020 | Jones et al. |
| 2008/0019906 | A1 | 1/2008 | Dimagno |
| 2008/0145763 | A1 | 6/2008 | Koh et al. |
| 2009/0310222 | A1 | 12/2009 | Pudleiner et al. |
| 2010/0092755 | A1 | 4/2010 | Pudleiner et al. |
| 2010/0099031 | A1 | 4/2010 | Kato et al. |
| 2010/0305368 | A1 | 12/2010 | Grubbs et al. |
| 2011/0076572 | A1 | 3/2011 | Amine et al. |
| 2011/0143219 | A1 | 6/2011 | Weiss et al. |
| 2012/0164541 | A1 | 6/2012 | Darolles et al. |
| 2015/0118579 | A1 | 4/2015 | Kondo et al. |
| 2015/0155598 | A1 | 6/2015 | Yazami |
| 2015/0303514 | A1 | 10/2015 | Nakamoto et al. |
| 2016/0024244 | A1 | 1/2016 | Xia et al. |
| 2016/0043440 | A1 | 2/2016 | Nakamoto et al. |
| 2016/0285129 | A1 | 9/2016 | Nakamoto et al. |
| 2016/0289392 | A1 | 10/2016 | Grubbs et al. |
| 2016/0356923 | A1 | 12/2016 | Miyake et al. |
| 2017/0018795 | A1 | 1/2017 | Nakamoto et al. |
| 2017/0018801 | A1 | 1/2017 | Grubbs et al. |
| 2017/0033359 | A1 | 2/2017 | Ogumi et al. |
| 2017/0057908 | A1 | 3/2017 | Jones et al. |
| 2020/0106133 | A1 | 4/2020 | Jones et al. |
| 2020/0373622 | A1 | 11/2020 | Jones et al. |

FOREIGN PATENT DOCUMENTS

| | | |
|---|---|---|
| CN | 102812586 | 12/2012 |
| CN | 103563154 | 2/2014 |
| CN | 103992275 | 8/2014 |
| DE | 102006015787 | 4/1985 |
| EP | 1039570 | 9/2000 |
| EP | 1718713 | 11/2006 |
| EP | 2133202 | 12/2009 |
| EP | 2157133 | 2/2010 |
| JP | 07-249432 | 9/1995 |
| JP | 2004-155729 | 6/2004 |
| JP | 2006221973 | 8/2006 |
| JP | 2010-238504 | 10/2010 |
| JP | 2011-023160 | 2/2011 |
| JP | 2012089704 | 5/2012 |
| JP | 2014-501434 | 1/2014 |
| JP | 2014-522077 | 8/2014 |
| JP | 2015-207357 | 11/2015 |
| JP | 2016-062821 | 4/2016 |
| WO | WO 1992/020446 | 11/1992 |
| WO | WO 2001/085869 | 11/2001 |
| WO | WO 2010/055762 | 5/2010 |
| WO | WO 2011/072166 | 6/2011 |
| WO | WO 2012/087414 | 6/2012 |
| WO | WO 2015/093272 | 6/2015 |
| WO | WO 2015/098766 | 7/2015 |
| WO | WO 2015/146265 | 10/2015 |

OTHER PUBLICATIONS

Brown et al. (1953) "Chemical effects of steric strains. VII. Strained homomorphs. III. Steric strains as a factor in the soivoiytic reactions of neopentyidimethyi- and dineopentyimethyi-carbinyi chiorides," Journal of the American Chemical Society. 75:10-14.

Brown et al. (1953) "Chemical effects of steric strains. VIII. Strained homomorphs. IV. Neopentyitrimethyiammonium ion as a strained homomorph; the rates of reaction of neopentyldimethylamine with aikyi iodides," Journal of the American Chemical Society. 75:14-16.

Brown et al. (1953) "Stereochemistry. XIX. Strained homomorphs. I. General summary," Journal of the American Chemical Society. 75:1-6.

Christe et al. (Oct. 1990) "Syntheses, properties, and structures of anhydrous tetramethylammonium fluoride and its 1: 1 adduct with trans-3-amino-2-buteneitrile," J. Am. Chem. Soc. 112:21.7619-7625.

Davis et al. (Dec. 2018) "Room-temperature cycling of metal fluoride electrodes: Liquid electrolytes for high-energy fluoride ion cells," Science 362(6419): 1144-1148.

Edson et al. (2012) "Hydroxide based decomposition pathways of alkytrimethylammonium cations," Journal of Membrane Science. 399-400:49-59.

Extended European Search Report corresponding to European Patent Application No. 16862629.9, dated Feb. 1, 2019.

Eyal et al. (1989) "Hydrofluoric Acid Extraction by TBP and by Amines: I. A Critical Review of the HF-H2O-Extractant System," Solvent Extraction and Ion Exchange. 7(6):951-969.—Abstract Provided Only.

Ford (1973) "Synthesis of trineopentylamine," Journal of Organic Chemistry. 38:20.3614-3615.

Gordin et al. (May 15, 2014) "Bis(2,2,2-trifluoroethyl) Ether as an Electrolyte Co-Solvent for Mitigating Self-Discharge in Li/S Batteries," ACS App. Materials & Interfaces, 6.11. 8006-8010.

Gross et al. (2002) "19F-NMR solid state investigations of monovalent alkali metal fluorides and tetra-alkylammonium fluorides," Journal of Fluorine Chemistry. 115:2. 193-199.

(56) References Cited

OTHER PUBLICATIONS

Grovenstein et al. (1964) "Carbanions. VII. Cleavage of 2,2-dimethylpropyl-2,2,2-triphenylQthyl-, and 3,3,3-triphenylpropyltrimethylammonium iodides by sodium in liquid ammonia," Journal of the American Chemical Society. 86:5.854-861.

Gutmann (1976) "Solvent effects on the reactivities of organometallic compounds," Coord. Chem. Rev., 18:225-255.

Haynes et al. (Jun. 2014) "Laboratory Solvents and Other Liquid Reagents," CRC Handbook of Chemistry and Physics 94 Ed., Section 15: Practical Laboratory Data, Laboratory Solvents and Other Liquid Reagents, pp. 15-13-15-22.

Ingold et al. (1933) "Influence of poles and polar linkings on the course pursued by elimination reactions, XI, Decomposition of quaternary ammonium hydroxides containing the tert-butylcarbinyl group," Journal of the Chemical Society. 67-68.

International Search Report with Written Opinion corresponding International Patent Application No. PCT/US2016/045645, dated Jun. 16, 2017.

Iwai et al. (1963) "Acetylenic compounds. XXXIV. Rearrangement of propargylammoniumhalide derivatives," Chemical & Pharmaceutical Bulletin. 11:12.1556-1563.

Long et al. (2012) "Hydroxide Degradation Pathways for Substituted Trimetliylammonium Cations: A DFT Study," Journal of Physical Chemistry. 115:17.9419-9426.

Mahjoub (1995) "Reactions of the 'naked' fluoride ion: syntheses and structures of SeF62- and BrF6-," Chemistry—A European Journal. 1:4.261-265.

Manecke et al. (1986) "Encyclopedia of Polymer Science and Engineering, 2nd Edition," John Wiley. 5:725-755.

Marino et al. (publicly available Nov. 2014) "Alkaline Stability of Quaternary Ammonium Cations for Alkaline Fuel Cell Membranes and Ionic Liquids," ChemSusChem. (Feb. 2015) 8(3): 513-523.

Pine et al. (1970) "Stevens rearrangements of N,N,N-trimethylneopentylammonium iodide," Journal of Organic Chemistry. 35:11.3663-3666.

Search Report corresponding International Patent Application No. PCT/US2016/045617, dated Jun. 15, 2017.

Sharma et al. (Jun. 1983) "Instability of anhydrous tetra-n-alkylammonium fluorides," J. Org. Chem., vol. 48, No. 12, pp. 2112-2114.

Stevens et al. (1941) "Mechanism of elimination reactions. I. The decomposition of quaternary ammonium bases and of xanthate esters," Journal of the American Chemical Society. 63:3132-3136.

Weng et al. (Jan. 20, 2013) "Ultrasound Assisted Design of S/C Cathodes with Partially Fluorinated Ether Electrolytes for Highly Efficient Li/S Batteries," Advanced Materials, 25.11. 1608-1615.

White et al. (1961) "The synthesis and certain reactions of nitroalkanes and nitro amines," United States Department of Commerce, Office of Technical Services. PB Report. 156.069.8.

Written Opinion corresponding International Patent Application No. PCT/US2016/045617, dated Jun. 15, 2017.

Wynn et al. (Nov. 1984) "The solubility of alkali-metal fluorides in non-aqueous solvents with and without crown ethers, as determined by flame emission spectroscopy," Talana, vol. 31, No. 11, pp. 1036-1040.

Zhang et al. (1995) "Fluorocarbonate, [FC02]-: preparation and structure," Angewandte Chemie. 34:17.1858-1860.

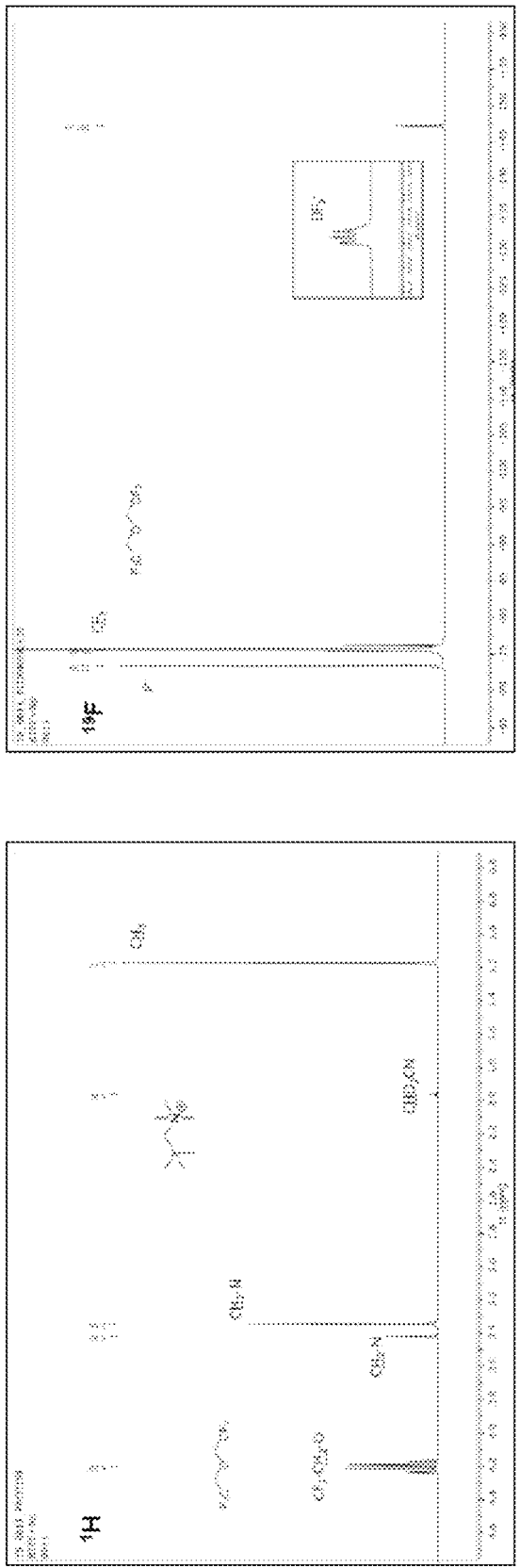
FIG. 6A
FIG. 6B

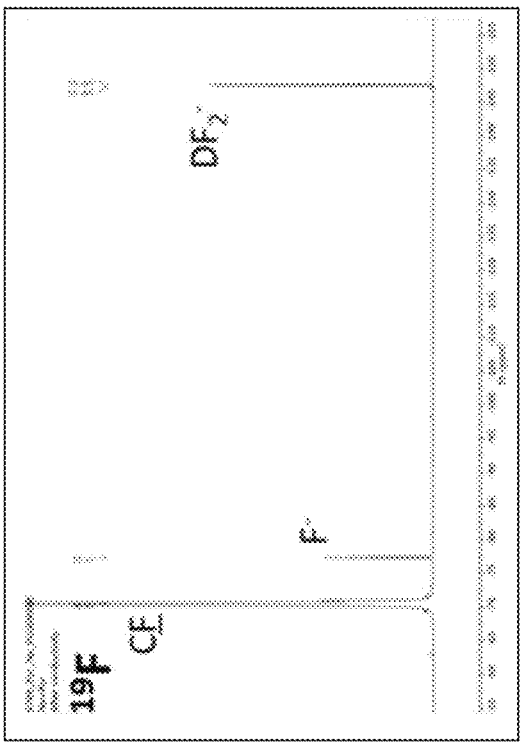
FIG. 7B
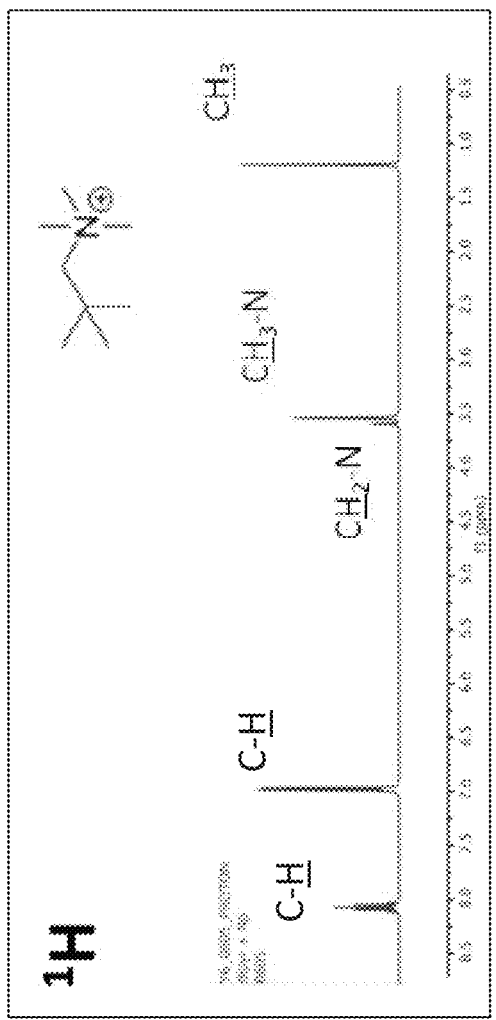
FIG. 7A
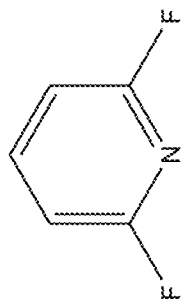
2,6-difluoropyridine (2,6-F$_2$Py);

Bis(2,2,2-trifluoroethyl)ether (BTFEC)

3-methoxypropionitrile (3MeOPN)

NON-AQUEOUS FLUORIDE SALTS, SOLUTIONS, AND THEIR USES

CROSS-REFERENCE TO RELATED APPLICATION(S)

This application is a continuation of U.S. Nonprovisional patent application Ser. No. 16/897,771 filed Jun. 10, 2020, which is a continuation of U.S. Nonprovisional patent application Ser. No. 15/228,876 filed Aug. 4, 2016 (now U.S. Pat. No. 10,720,666), which claims the benefit of and priority to U.S. Provisional Application No. 62/200,998, filed on Aug. 4, 2015, each of which is incorporated herein by reference.

GOVERNMENT SUPPORT

The invention described herein was made in the performance of work under a NASA contract NNN12AA01C, and is subject to the provisions of Public Law 96-517 (35 USC 202) in which the Contractor has elected to retain title.

BACKGROUND

A battery generally includes a positive electrode (cathode during discharge), a negative electrode (anode during discharge), and an electrolyte for ion transport therebetween. The electrolyte can contain one or more ionic species that act as charge carriers. Many widely available battery systems are based on cation electrode reactions, with electrodes capturing or releasing a cation from an electrolyte and balancing the charge with an electron from the external circuit. Because of its very low electrochemical oxidation/reduction potential and light weight, the element lithium (Li) is commonly used in cation based battery systems. Both lithium and Li-ion batteries are commercially available and widely used.

However, the electrochemistry of lithium metal or lithium-containing electrodes presents problems for commercial use. In one aspect, lithium metal is highly reactive and safeguards are used to store lithium in safe forms (e.g., intercalates), increasing battery weight and reducing energy density. For example, individual Li-ion batteries and Li-ion battery packs often contain expensive voltage and thermal control circuitry to shut down the battery when voltage or temperature is outside an optimal operating range.

Fluoride-anion based electrode reactions offer an alternative to lithium and lithium-ion batteries. For example, in a fluoride ion battery (FIB), an anode and cathode are physically separated from one another but in common contact with a fluoride anion conducting electrolyte. The anode and cathode are typically formed from low potential elements or compounds (e.g., metals, metal fluorides, or intercalating compositions such as graphite or other carbon based material), where the cathode material possesses a higher potential than the anode material. Fluoride anions ($F^-$) in the fluoride anion conducting electrolyte move from the cathode to the anode during discharge and from the anode to the cathode during charge of the battery.

Notably, operation of such fluoride ion batteries requires a ready source of mobile $F^-$ in the electrolyte for operation. However, many solid-state electrolyte compositions have poor ionic conductivity at temperatures below about 200° C., resulting in significant reduction in cell performance at lower temperatures due to high cell internal resistance. Furthermore, common metal fluorides (e.g., LiF, CsF, $MgF_2$, $BaF_2$), transition metal fluorides (e.g., $VF_4$, $FeF_3$, $MoF_6$, $PdF_2$, AgF), main group metal fluoride (e.g., $AlF_3$, $PbF_4$, $BiF_3$) and lanthanide or actinide fluorides (e.g., $LaF_3$, $YF_3$, $UF_5$) are largely insoluble in organic solvents and cannot be used as liquid electrolyte components.

Accordingly, there exists an ongoing need for improved fluoride-based electrolytes for use in electrochemical applications.

SUMMARY

Embodiments of the disclosure provide anhydrous fluoride salts, optionally anhydrous, lithium-free fluoride salts, and non-aqueous solutions thereof. Fluoride salt and non-aqueous solvent combinations, for example, are provided that possess high fluoride ion concentrations that are useful for a range of applications, including electrolytes for electrochemical systems. Electrochemical systems are provided incorporating a non-aqueous electrolyte component characterized by high concentrations of fluoride ions, including fluoride-ion battery systems, optionally, lithium-free fluoride-ion battery systems.

In some embodiments, the molecular structure of the fluoride salt facilitates their ability to (i) be made in anhydrous form without substantial decomposition and (ii) to achieve efficient dissociation to generate high fluoride ion concentrations in non-aqueous solvents. For example, fluoride salts useful for some applications include one or more fluoride ions and an organic cation (e.g., having a charge center of N, P, S, or O) that does not possess a carbon in the β-position or does not possess a carbon in the β-position having a bound hydrogen. In certain embodiments, the organic cation does not possess an $sp^3$-hybridized carbon in the β-position having a bound hydrogen. Examples of fluoride salts may include, but are not limited to, ammonium salts including alkyl ammonium salts such as (2,2-dimethylpropyl)trimethylammonium fluoride ($NpMe_3NF$) and bis (2,2-dimethylpropyl)dimethylammonium fluoride ($Np_2Me_2NF$).

Embodiments of the disclosure provide non-aqueous solutions of these fluoride salts characterized by high fluoride ion concentrations in one or more non-aqueous solvents (e.g., greater than or equal to 0.05 M and, in certain cases, up to 20 M). The fluoride salts are anhydrous prior to contact with the non-aqueous solvents to form electrolyte solutions. That is, the fluoride salts are not formed in-situ within the electrolyte. As discussed in greater detail below, it has been identified that the combination of these fluoride salts with at least one fluorine-containing, non-aqueous solvent promotes dissociation and solubility of the fluoride salts within the non-aqueous solvents. Without being bound by theory, for example, it is believed that solvents having structures including $CH_2$ moieties adjacent to electron-withdrawing groups (e.g., O and/or $CF_3$) give rise to increased partial positive charge on the $CH_2$ moieties. The partial positive charge on the $CH_2$ moieties further promotes fluoride ion and cation solvation and attendant solubility of the fluoride salts.

For example, as discussed in greater detail below, theoretical calculations comparing the solvation free energies of fluoride ions and different cations in solvents with and without $CH_2$ moieties (e.g., characterized by the form $X-CH_2-Y-CH_2-X$ or $X-(CH_2)_2-Y-(CH_2)_2-X$, where X, Y are electron-withdrawing groups), illustrates that solvents lacking $CH_2$ moieties exhibit a pronounced decrease in fluoride solubility. Furthermore, solvents having structures including $CH_2$ moieties adjacent to electron withdrawing groups exhibit up to a ten-fold increase in the fluoride solvation free energy as compared to solvents lacking $CH_2$ moieties adjacent to electron withdrawing groups. Additionally, the presence of electron density modifying groups, such as electron donating and/or electron withdrawing groups, adjacent to the cation charge center may modify the attraction of the cation to the solvent, allowing the cation to be tuned to different solvents for enhanced solubility.

Non-aqueous solutions of the disclosed embodiments are compatible with a range of fluorinated and non-fluorinated solvents. Examples of the fluorinated, non-aqueous solvents may include, but are not limited to, bis(2,2,2-trifluoroethyl) ether (BTFE). In further embodiments, the solvent may be a mixture of at least one non-aqueous fluorine-containing solvent (e.g., BTFE) and at least one non-aqueous, non-fluorine containing solvent (e.g., propionitrile (PN), dimethoxyethane (DME)). For example, as discussed in detail below, electrolyte solutions including solvent mixtures of BTFE/PN are observed to exhibit higher conductivity than pure BTFE at the same molarity. Without being bound by theory, it is believed that solvents such as BTFE can charge separate and/or dissolve the fluoride salt in high concentration as ion pairs, whereas solvents such as PN dissociate the salt but are not polar enough to dissolve the salt in comparable concentrations in pure solvent.

Additional embodiments of the disclosure present use of these high concentration electrolyte solutions in electrochemical applications such as fluoride-ion batteries, electrochemical double-layer capacitors, and electrochemical fluorination reactions such as intercalation reactions.

In an embodiment, an electrolyte solution is provided. The solution includes a fluoride salt and one or more non-aqueous solvents, for example fluorinated solvents, non-fluorinated, non-aqueous solvents, or combinations thereof. The fluoride salt includes one or more fluoride ions and an organic cation, where the organic cation does not possess a carbon in the β-position or does not possess a carbon in the β-position having a bound hydrogen, and the cation charge center is N, P, S, or O. The concentration of said fluoride ions dissolved in said electrolyte solution is greater than or equal to 0.05 M Embodiments of the electrolyte solution may include one or more of the following, in any combination.

In an embodiment, the organic cation does not possess a carbon in the β-position or does not possess an $sp^3$-hybridized carbon in the β-position having a bound hydrogen.

In an embodiment of the electrolyte solution, the concentration of said fluoride ions dissolved in said electrolyte solution is greater than or equal to 1 M. In an embodiment of the electrolyte solution, the concentration of fluoride ions dissolved in the electrolyte solution is selected over the range of 0.5 M to 20 M.

In an embodiment of the electrolyte solution, the fluoride salt is provided to said non-aqueous solvent in an anhydrous form. In an embodiment of the electrolyte solution, the fluoride salt does not include lithium.

In an embodiment of the electrolyte solution, the fluoride salt is a substituted or unsubstituted ammonium fluoride salt. The substituted or unsubstituted ammonium fluoride salt includes a substituted or unsubstituted alkylammonium cation characterized by the formula (FX1):

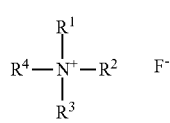

(FX1)

where each of $R^1$, $R^2$, $R^3$, and $R^4$ is independently a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{ao}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl, halo; or where at least two of $R^1$-$R^4$ combine to form one or more alicyclic or aromatic, carbocyclic or heterocyclic 5 or 6 membered rings.

In an embodiment of the electrolyte solution, at least one of $R^1$, $R^2$, $R^3$, and $R^4$ is independently a halogen-substituted substituent.

In an embodiment of the electrolyte solution, at least one of $R^1$, $R^2$, $R^3$, and $R^4$ is independently a fluorine-substituted substituent.

In an embodiment of the electrolyte solution, at least one of $R^1$, $R^2$, $R^3$, and $R^4$ independently is a polar substituent.

In an embodiment of the electrolyte solution, at least one of $R^1$, $R^2$, $R^3$, and $R^4$ is independently a polar group selected from the group consisting of substituted or unsubstituted phenyl, benzyl, or heterocyclic species.

In an embodiment of the electrolyte solution, the ammonium fluoride salt is characterized by the formula (FX2a), (FX2b), (FX2c), or (FX2d):

(FX2a)

(FX2b)

(FX2c)

(FX2d)

In an embodiment of the electrolyte solution, the ammonium fluoride salt is a substituted or unsubstituted neo-pentyl ammonium fluoride salt. For example, in an embodiment, the substituted or unsubstituted neo-pentyl ammonium fluoride salt is characterized by the formula (FX3a), (FX3b), (FX3c), or (FX3d):

(FX3a)

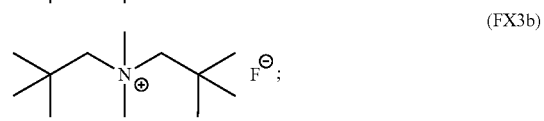

(FX3b)

-continued

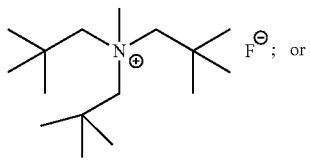 (FX3c)

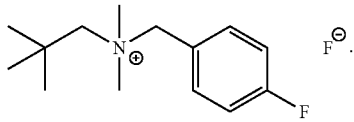 (FX3d)

In another embodiment of the electrolyte solution, the ammonium fluoride salt is a substituted or unsubstituted benzylammonium cation. In an embodiment, the substituted or unsubstituted benzylammonium cation is characterized by the formula (FX4a) or (FX4b):

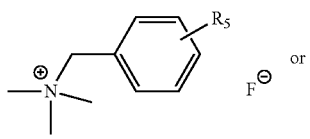 (FX4a)

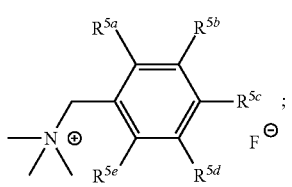 (FX4b)

where $R^5$ is $O-R^6$, $N-R^6$, $CO_2-R^6$, $CF_3$, $SF_5$, or $-SO_2R^6$, $R^{5a}-R^{5e}$ are independently selected from H, $O-R^6$, $N-R^6$, $CO_2-R^6$, $CF_3$, $SF_5$, or $-SO_2R^6$, and $R^6$ is H, $C_1$-$C_{10}$ alkyl, or $C_1$-$C_{10}$ aryl.

In an embodiment of the electrolyte solution, $R^5$ is one of $N-(CH_3)_2$, $O-CH_3$, $CO_2-CH_3$, or $CF_3$. In an embodiment of the electrolyte solution, $R^6$ is a $C_1$-$C_{10}$ fluorocarbon (e.g., $CF_3$ or $C_2F_5$).

In another embodiment of the electrolyte solution, the fluoride salt is a substituted or unsubstituted hexamethylenetetramine (HMT) fluoride salt.

In another embodiment of the electrolyte solution, the hexamethylenetetramine (HMT) fluoride salt is characterized by the formula (FX5a), (FX5b), (FX5c), (FX5d):

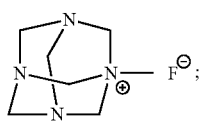 (FX5a)

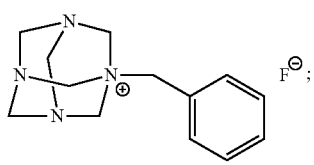 (FX5b)

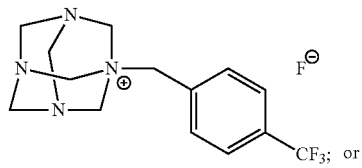 (FX5c)

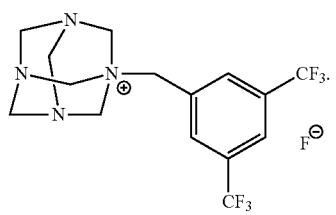 (FX5d)

In another embodiment, the fluoride salt is a substituted or unsubstituted, saturated or unsaturated heterocyclic fluoride salt, where the heterocyclic cation includes one or more nitrogen, oxygen, sulfur, or phosphorous atoms as part of a four-, five-, six-, or seven-membered ring, where one or more of the heterocyclic cations bears a formal charge conferred through alkylation of the heterocyclic cation, and the heterocyclic cation does not possess a carbon in the β position or does not possess an $sp^3$-hybridized carbon in the β position having a bound hydrogen.

In another embodiment, the heterocyclic fluoride salt is characterized by the formula (FX6a), (FX6b), (FX6c), (FX6d), (FX6e), (FX6f), (FX6g), (FX6h), or (FX6i):

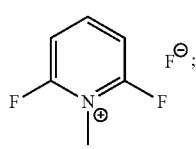 (FX6a)

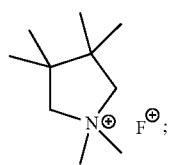 (FX6b)

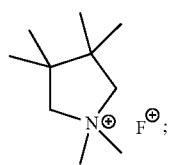 (FX6c)

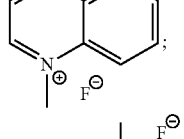 (FX6d)

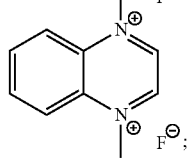

-continued

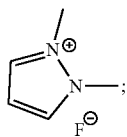
(FX6f)

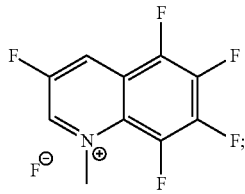
(FX6g)

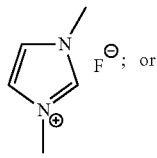
(FX6h)

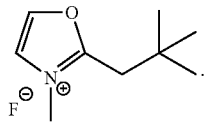
(FX6i)

In another embodiment of the electrolyte solution, the non-aqueous solvent is one or more fluorinated non-aqueous solvent.

In another embodiment of the electrolyte solution, the non-aqueous solvent characterized by the form [X—(CH$_2$)$_n$—Y], where n=1 or 2, where X and Y are electron withdrawing functional groups having a combined effect to confer a partial positive charge on the CH$_2$ group or groups.

In another embodiment of the electrolyte solution, Y is O or S and X is a functional group selected from the group consisting of ethers, esters, acid anhydrides, amines, amides, carbonates, sulfones, sulfonyl esters, phosphites, phosphates, nitriles, nitro, aldehydes, acetates, SF$_5$, or fluorocarbons (e.g., —CF$_3$, —CF$_2$CF$_3$).

In another embodiment of the electrolyte solution, the non-aqueous solvent is an aromatic solvent including at least one functional group characterized by the form [X—(CH$_2$)$_n$—Y], where n=1 or 2 and where X and Y are polar functional groups having a combined effect to confer a partial positive charge on the CH$_2$ group or groups.

In another embodiment of the electrolyte solution, Y is O or S and X is a functional group selected from the group consisting of ethers, esters, acid anhydrides, amines, amides, carbonates, sulfones, sulfonyl esters, phosphites, phosphates, nitriles, nitro, aldehydes, acetates, SF$_5$, or fluorocarbons (e.g., —CF$_3$, —CF$_2$CF$_3$).

In another embodiment of the electrolyte solution, the non-aqueous solvent is a fluorinated ether and any combination thereof. For example, in an embodiment, the fluorinated ether is characterized by the formula (FX7a) (FX7b), (FX7c), (FX7d), (FX7e), (FX7f), or (FX7g):

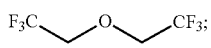
(FX7a)

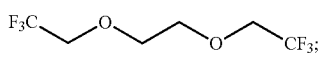
(FX7b)

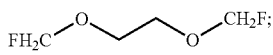
(FX7c)

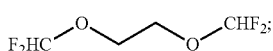
(FX7d)

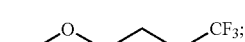
(FX7e)

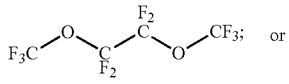
(FX7f)

(FX7g)

In an embodiment of the electrolyte solution, the non-aqueous solvent is a fluorinated phosphite and any combination thereof. For example, in an embodiment, the fluorinated phosphite is characterized by the formula (FX8a):

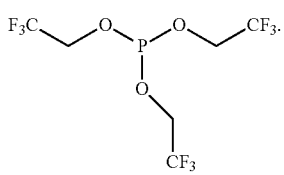
(FX8a)

In another embodiment of the electrolyte solution, the non-aqueous solvent is a fluorinated ester or anhydride and any combination thereof. For example, in an embodiment, the fluorinated ester or anhydride is characterized by the formula (FX9a), (FX9b), or (FX9c):

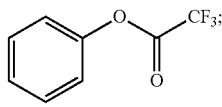
(FX9a)

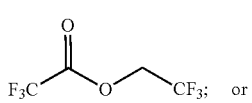
(FX9b)

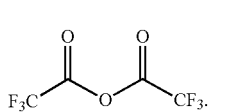
(FX9c)

In another embodiment of the electrolyte solution, the non-aqueous solvent is a nitrile and any combination thereof. For example, in an embodiment, the nitrile is characterized by the formula (FX10a), (FX10b), (FX10c), or (FX10d):

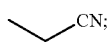
(FX10a)

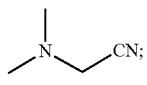
(FX10b)

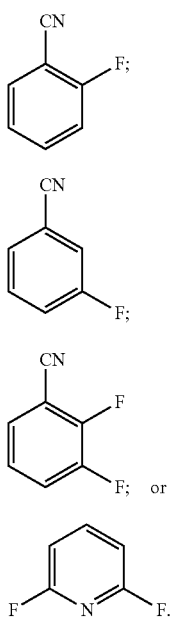

In another embodiment of the electrolyte solution, the non-aqueous solvent is a fluorine-substituted aromatic solvent and any combination thereof. For example, in an embodiment, the fluorine-substituted aromatic is characterized by the formula (FX11a), (FX11b), (FX11c), or (FX11d):

In another embodiment of the electrolyte solution, the non-aqueous solvent is characterized by the formula (FX12a) or (FX12b) and any combination thereof:

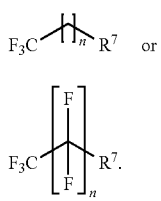

where $R^7$ is a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl or halo; or where at least two of $R^1$-$R^4$ combine to form one or more alicyclic or aromatic, carbocyclic or heterocyclic 5 or 6 membered rings and where n is an integer selected from the range of 1 to 20.

In a further embodiment, an electrolyte solution is provided. The electrolyte solution includes a fluoride salt and a non-aqueous solvent mixture including a first non-aqueous fluorine-containing solvent and a second, non-aqueous solvent, different from the first solvent. The fluoride salt includes one or more fluoride ions and an organic cation, where the organic cation does not possess a carbon in the β-position or does not possess a carbon in the β-position having a bound hydrogen, and the cation charge center is N, P, S, or O. The concentration of the fluoride ions dissolved in the electrolyte solution is greater than or equal to 0.05 M.

Embodiments of the electrolyte solution may include one or more of the following, in any combination.

In another embodiment of the electrolyte solution, the concentration of the fluoride ions dissolved in the electrolyte solution is greater than or equal to 1 M. In another embodiment of the electrolyte solution, the concentration of fluoride ions dissolved in the electrolyte solution is selected over the range of 0.05 M to 20 M.

In another embodiment of the electrolyte solution, the second, non-aqueous solvent is a non-fluorine containing solvent.

In another embodiment of the electrolyte solution, second, non-aqueous solvent is a fluorine-containing solvent.

In another embodiment of the electrolyte solution, a ratio of amounts of the first solvent and the second solvent is greater than 1:2. In another embodiment of the electrolyte solution, a ratio of amounts of the first solvent and the second solvent is selected from the range from 1:20 to 20:1 and, optionally, from 1:2 to 9:1.

In another embodiment of the electrolyte solution, the first solvent and the second solvent are each independently a polar solvent.

In another embodiment of the electrolyte solution, the first solvent, the second solvent, or both is independently selected from the group consisting of ethers, esters, acid anhydrides, amines, amides, carbonates, sulfones, sulfonyl esters, phosphites, phosphates, nitriles, or glymes.

In an embodiment of the electrolyte solution, the first solvent, the second solvent, or both is independently an aromatic solvent.

In another embodiment of the electrolyte solution, the first solvent is a fluorinated ether. For example, the fluorinated ether is characterized by the formula (FX7a) or (FX7b), (FX7c), (FX7d), (FX7e), (FX7f), or (FX7g):

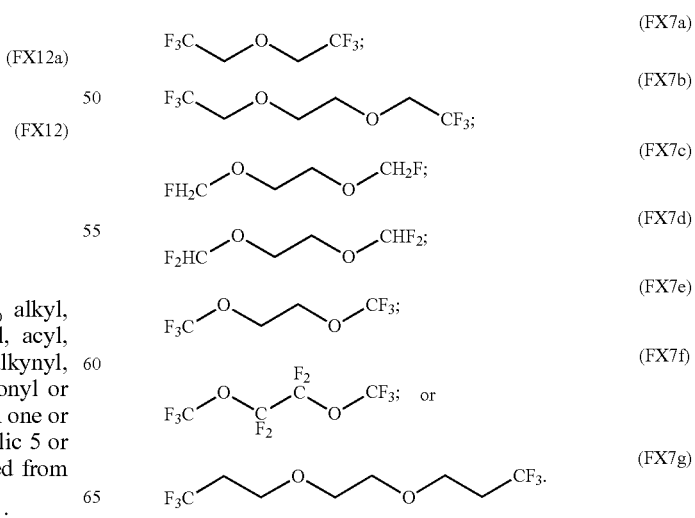

In another embodiment of the electrolyte solution, the first solvent is a fluorinated phosphite. For example, in an embodiment, the fluorinated phosphite is characterized by the formula (FX8a):

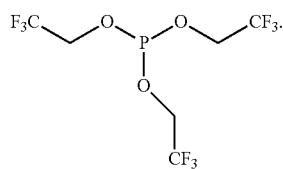
(FX8a)

In another embodiment of the electrolyte solution, the first solvent is a fluorinated ester or anhydride. For example, in an embodiment, the fluorinated ester or anhydride is characterized by the formula (FX9a), (FX9b), or (FX9c):

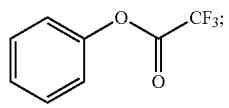
(FX9a)

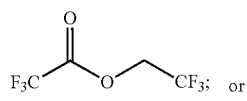
(FX9b)

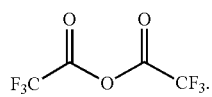
(FX9c)

In another embodiment of the electrolyte solution, the first solvent is a fluorinated nitrile. For example, in an embodiment, the fluorinated nitrile is characterized by the formula (FX10c):

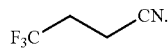
(FX10c)

In another embodiment of the electrolyte solution, the first solvent is a fluorinated aromatic solvent. For example, in an embodiment, the fluorinated aromatic solvent is characterized by the formula (FX11a), (FX11b), (FX11c), or (FX11d):

(FX11a)

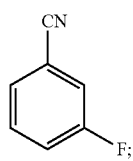
(FX11b)

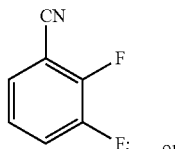
(FX11c)

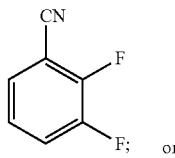
(FX11d)

In another embodiment of the electrolyte solution, the second solvent is selected from the group consisting of: nitriles, benzonitriles, pyridines, and esters.

In another embodiment of the electrolyte solution, the second solvent is a nitrile characterized by the formula (FX10a), (FX10b), or (FX10d):

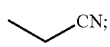
(FX10a)

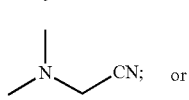
(FX10b)

(FX10d)

In an embodiment of the electrolyte solution, the second solvent is a substituted or unsubstituted benzonitrile characterized by the formula (FX13a) or (FX13b):

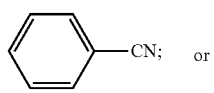
(FX13a)

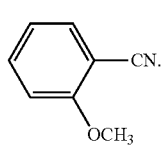
(FX13b)

In an embodiment of the electrolyte solution, the first solvent is characterized by the formula (FX7a):

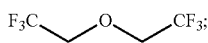
(FX7a)

and the second solvent is characterized by the formula (FX10a):

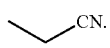
(FX10a)

In an embodiment of the electrolyte solution, the fluoride salt includes a substituted or unsubstituted ammonium fluoride salt.

In an embodiment of the electrolyte solution, the substituted or unsubstituted ammonium fluoride salt includes a substituted or unsubstituted alkylammonium cation characterized the formula (FX1): $R^1R^2R^3R^4N^+$ (FX1), where each of $R^2$, $R^3$, and $R^4$ is independently a substituted or unsubstituted $C_1$-$C_{20}$ alkyl, $C_3$-$C_{20}$ cycloalkyl, $C_5$-$C_{30}$ aryl, $C_5$-$C_{30}$ heteroaryl, Cao acyl, $C_2$-$C_{20}$ alkenyl, $C_3$-$C_{20}$ cycloalkenyl, $C_2$-$C_{20}$ alkynyl, $C_5$-Cao alkylaryl, $C_1$-$C_{20}$ alkyl, $C_2$-$C_{20}$ alkoxycarbonyl, or halo; or where at least two of $R^1$-$R^4$ combine to form one or more alicyclic or aromatic, carbocyclic or heterocyclic 5 or 6 membered rings.

In an embodiment of the electrolyte solution, at least one of $R^1$, $R^2$, $R^3$, and $R^4$ is independently a halogen substituted substituent.

In an embodiment of the electrolyte solution, at least one of $R^1$, $R^2$, $R^3$, and $R^4$ is independently a fluorine substituted substituent.

In an embodiment of the electrolyte solution, at least one of $R^1$, $R^2$, $R^3$, and $R^4$ independently is a polar substituent.

In an embodiment of the electrolyte solution, at least one of $R^1$, $R^2$, $R^3$, and $R^4$ is independently a polar group selected from the group consisting of substituted or unsubstituted phenyl, benzyl, or heterocyclic species.

In an embodiment of the electrolyte solution, the ammonium fluoride salt is characterized by the formula (FX 2a); (FX2b), (FX2c), or (FX2d):

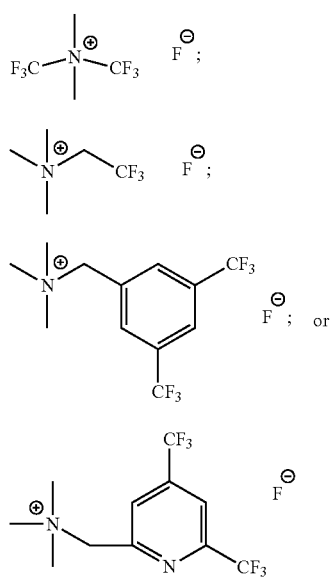

In an embodiment of the electrolyte solution, the ammonium fluoride salt is a substituted or unsubstituted neo-pentyl ammonium fluoride salt.

In an embodiment of the electrolyte solution, the substituted or unsubstituted neo-pentyl ammonium fluoride salt is characterized by the formula (FX3a), (FX3b), (FX3c), or (FX3d):

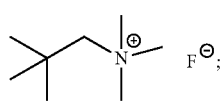

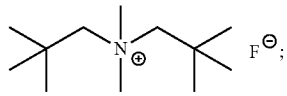

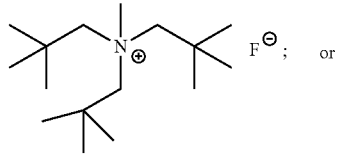

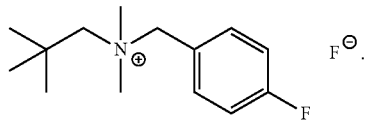

In an embodiment of the electrolyte solution, the ammonium fluoride salt comprises a substituted or unsubstituted benzylammonium cation.

In an embodiment of the electrolyte solution, the substituted or unsubstituted benzylammonium cation is characterized by the formula (FX4a) or (FX4b):

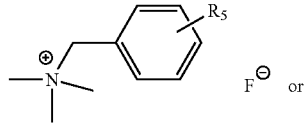

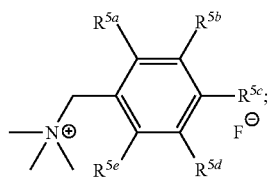

where $R^5$ is O—$R^6$, N—$R^6$, $CO_2$—$R^6$, $CF_3$, $SF_5$, or —$SO_2R^6$, $R^{5a}$-$R^{5e}$ are independently selected from H, O—$R^6$, N—$R^6$, $CO_2$—$R^6$, $CF_3$, $SF_5$, or —$SO_2R^6$, and $R^6$ is H, $C_1$-$C_{10}$ alkyl, or $C_1$-$C_{10}$ aryl.

In an embodiment of the electrolyte solution, $R^5$ is one of N—$(CH_3)_2$, O—$CH_3$, $CO_2$—$CH_3$ or $CF_3$. In an embodiment of the electrolyte solution, $R^6$ is a $C_1$-$C_{10}$ fluorocarbon (e.g., $CF_3$ or $C_2F_5$).

In an embodiment of the electrolyte solution, the fluoride salt includes a substituted or unsubstituted hexamethylenetetramine (HMT) fluoride salt.

In an embodiment of the electrolyte solution, the hexamethylenetetramine (HMT) fluoride salt is characterized by the formula (FX5a), (FX5b), (FX5c), or (FX5d):

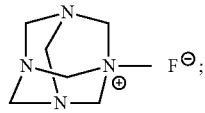

-continued

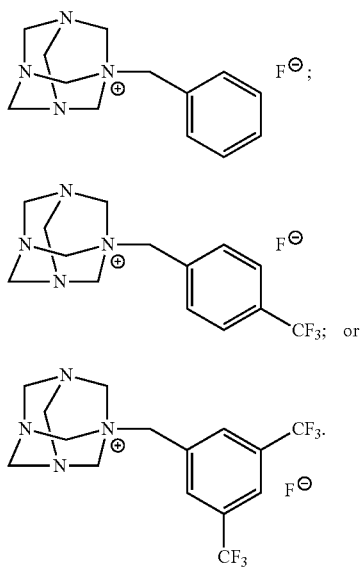

(FX5b)

(FX5c)

(FX5d)

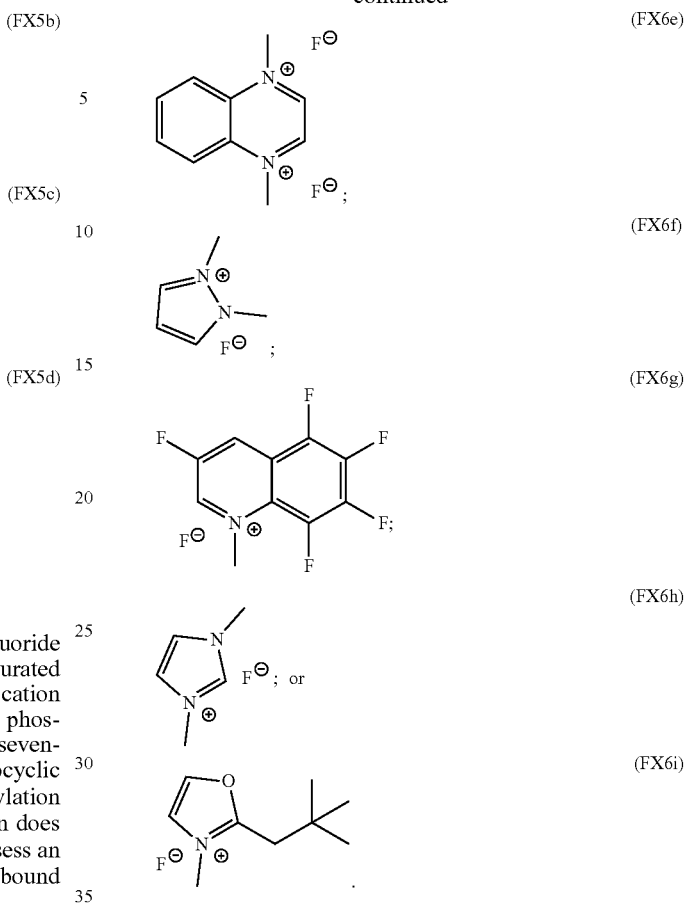

(FX6a)

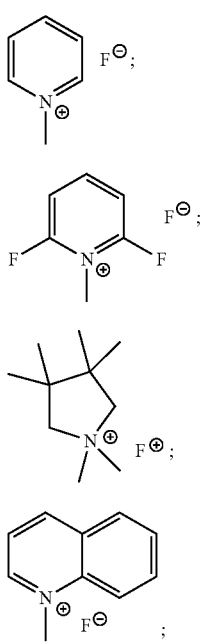

(FX6b)

(FX6c)

(FX6d)

(FX6e)

(FX6f)

(FX6g)

(FX6h)

(FX6i)

In an embodiment of the electrolyte solution, the fluoride salt is a substituted or unsubstituted, saturated or unsaturated heterocyclic fluoride salt, where the heterocyclic cation comprises one or more nitrogen, oxygen, sulfur, or phosphorus atoms as part of a four-, five-, six-, or seven-membered ring, where one or more of the heterocyclic cations bears a formal charge conferred through alkylation of the heterocyclic cation, and the heterocyclic cation does not possess a carbon in the β position or does not possess an sp$^3$-hybridized carbon in the β position having a bound hydrogen.

In an embodiment of the electrolyte solution, the heterocyclic fluoride salt is characterized by the formula (FX6a), (FX6b), (FX6c), (FX6d), (FX6e), (FX6f), (FX6g), (FX6h), or (FX6i):

In a further embodiment, an electrochemical cell is provided. The electrochemical cell includes a positive electrode, a negative electrode, and an electrolyte solution provided between the positive electrode and the negative electrode. The electrolyte solution includes a fluoride salt and one or more non-aqueous solvents. The fluoride salt includes one or more fluoride ions and an organic cation. The organic cation does not possess a carbon in the β-position or does not possess a carbon in the β-position having a bound hydrogen, and the cation charge center is N, P, S, or O. The concentration of the fluoride ions dissolved in the electrolyte solution is greater than or equal to 0.05 M.

In an embodiment, an electrochemical cell is provided. The electrochemical cell includes a positive electrode, a negative electrode, and an electrolyte solution provided between the positive electrode and the negative electrode. The electrolyte solution includes a fluoride salt and a non-aqueous solvent mixture. The fluoride salt includes one or more fluoride ions and an organic cation. The organic cation does not possess a carbon in the β-position or does not possess a carbon in the β-position having a bound hydrogen, and the cation charge center is N, P, S, or O. The non-aqueous solvent mixture includes a first non-aqueous, fluorine-containing solvent and a second, non-aqueous solvent, different from the first solvent. The concentration of fluoride ions dissolved in the electrolyte solution is greater than or equal to 0.05 M.

Embodiments of any of the electrochemical cells may include one or more of the following, in any combination.

In an embodiment of the electrochemical cell, the concentration of the fluoride ions dissolved in the electrolyte solution is greater than or equal to 1 M.

In an embodiment of the electrochemical cell, the concentration of the fluoride ions dissolved in the electrolyte solution is selected over the range of 0.05 M to 20 M.

In another embodiment of the electrochemical cell, the second, non-aqueous solvent is a non-fluorine containing solvent.

In another embodiment of the electrochemical cell, second, non-aqueous solvent is a fluorine-containing solvent.

In an embodiment of the electrochemical cell, the electrolyte solution provides for transport of fluoride ions between said positive electrode and the negative electrode.

In an embodiment of the electrochemical cell, the electrolyte solution provides a conductivity of fluoride ions greater than or equal to 0.1 mS/cm at 25 C.

In an embodiment of the electrochemical cell, the electrolyte solution does not include lithium.

In an embodiment, the electrochemical cell does not include lithium.

In an embodiment, the electrochemical cell includes a fluoride-ion electrochemical cell.

In an embodiment, the electrochemical cell includes a secondary electrochemical cell.

In an embodiment, the electrochemical cell includes a battery, a fuel cell, an electrolysis system, or a capacitor.

In an additional embodiment, an electrolyte solution is provided. The electrolyte solution includes a first fluoride salt, a second fluoride salt, and one or more non-aqueous solvents. The first fluoride salt includes one or more fluoride ions and an organic cation, where the organic cation does not possess a carbon in the β-position or does not possess a carbon in the β-position having a bound hydrogen, and the cation charge center is N, P, S, or O. The second fluoride salt is different than the first fluoride salt and includes one or more fluoride ions and an organic cation, where the cation charge center is N, P, S, or O. The concentration of the fluoride ions dissolved in the electrolyte solution is greater than or equal to 0.05 M.

Embodiments of the electrolyte solution may include one or more of the following, in any combination.

In an embodiment of the electrolyte solution, the first fluoride salt includes a substituted or unsubstituted ammonium fluoride salt and the second fluoride salt includes a substituted or unsubstituted ammonium fluoride salt.

In an embodiment of the electrolyte solution, the second fluoride salt is characterized by tetramethylammonium fluoride (TMAF) or the formula (FX2a):

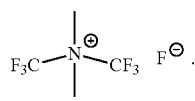

(FX2a)

In an embodiment of the electrolyte solution, the first ammonium fluoride salt is characterized by the formula (FX2b), (FX2c), (FX3a), (FX3b), (FX4a), (FX5a), (FX5b), (FX5c), or (FX5d):

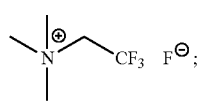

(FX2b)

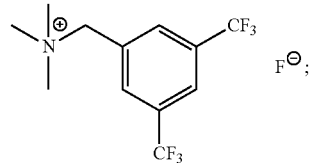

(FX2c)

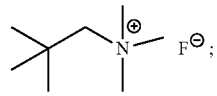

(FX3a)

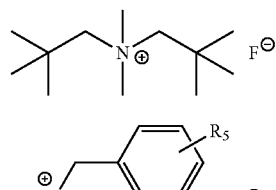

(FX3b)

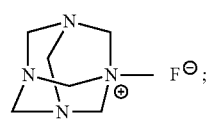

(FX4a)

(FX5a)

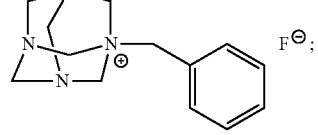

(FX5b)

(FX5c)

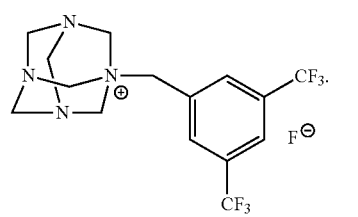

(FX5d)

In an embodiment of the electrolyte solution, the organic cation of the second fluoride salt does not possess a carbon in the β-position or does not possess a carbon in the β-position having a bound hydrogen.

In an embodiment of the electrolyte solution, the second ammonium fluoride salt is characterized by the formula (FX2b), (FX2c), (FX3a), (FX3b), (FX4a), (FX5a), (FX5b), (FX5c), (FX5d):

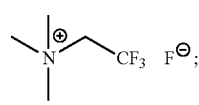

(FX2b)

-continued (FX2c)
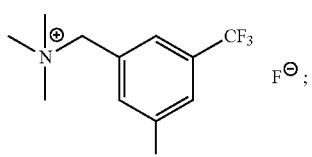

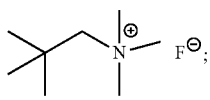 (FX3a)

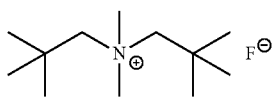 (FX3b)

(FX4a)
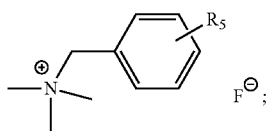

(FX5a)
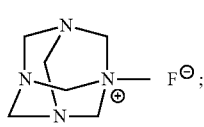

(FX5b)
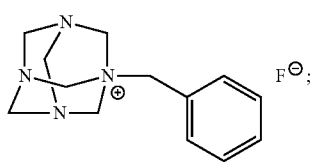

(FX5c)
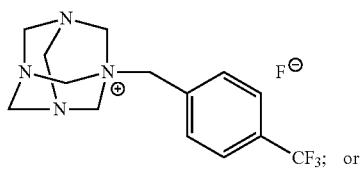

(FX5d)
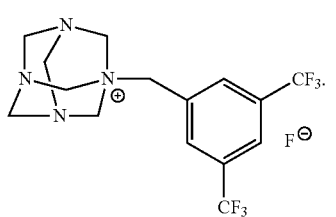

In an embodiment of the electrolyte solution, the first ammonium fluoride salt is characterized by the formula (FX2b), (FX2c), (FX3a), (FX3b), (FX4a), (FX5a), (FX5b), (FX5c), or (FX5d):

(FX2b)
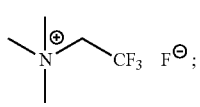

-continued (FX2c)
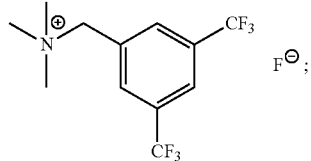

(FX3a)
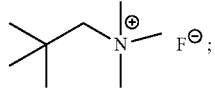

(FX3b)
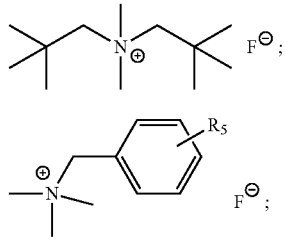

(FX4a)
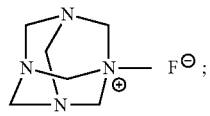

(FX5a)
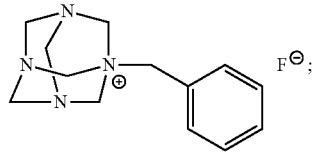

(FX5b)
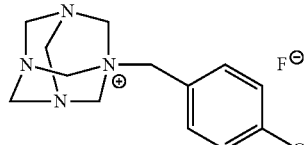

(FX5c)
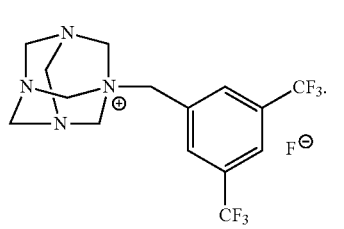

(FX5d)
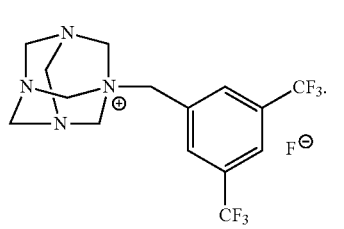

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIGS. 6A-6B are $^1$H and $^{19}$F NMR spectra of a solution of NpMe$_3$NF and bis(2,2,2-trifluoroethyl)ether (BTFE);

FIGS. 7A-7B are $^1$H and $^{19}$F NMR spectra of a solution of NpMe$_3$NF and 2,6-difluoropyridine (2,6-F$_2$Py);

DETAILED DESCRIPTION

Figure 1:
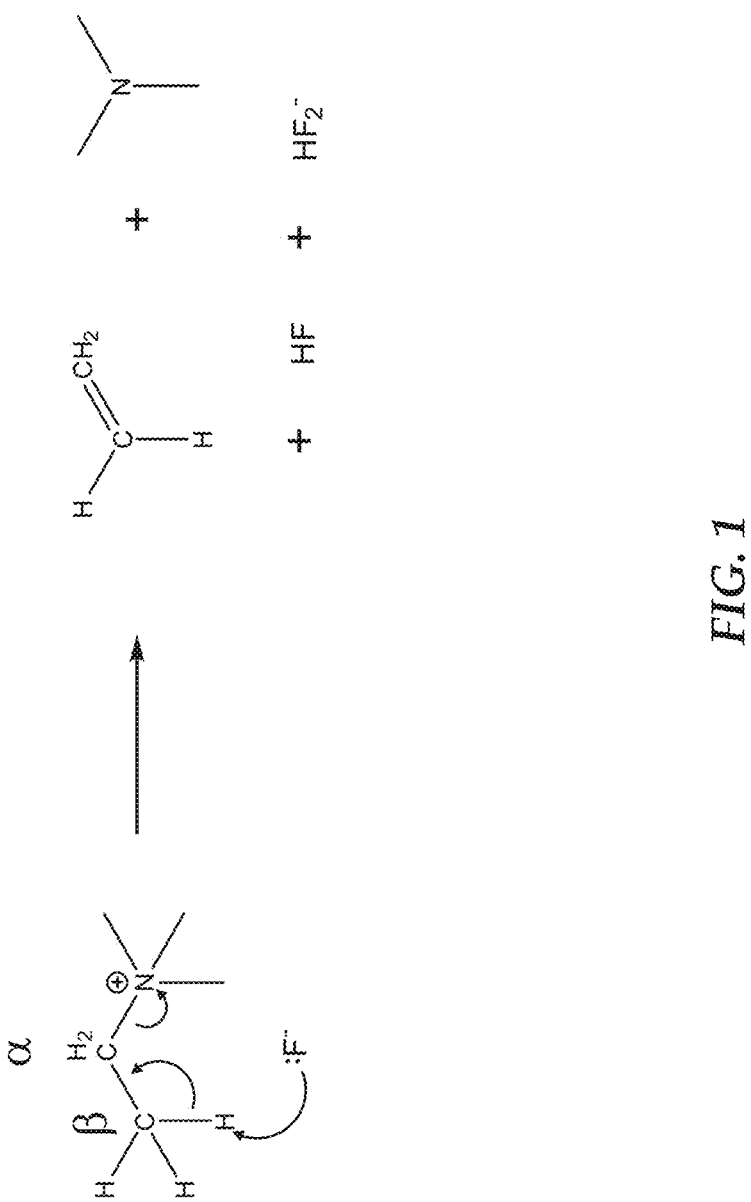
FIG. 1 is an illustration of decomposition of a tetraalkylammonium fluoride salt under drying conditions to form HF and $HF_2^-$.

In general, the terms and phrases used herein have their art-recognized meaning, which can be found by reference to standard texts, journal references and contexts known to those skilled in the art. The following definitions are provided to clarify their specific use in the context of the disclosed embodiments.

"Carbon in the β-position" or "β-carbon" refers to a carbon atom one removed from an atom, group, functional group, or other moiety of interest. In certain embodiments, the functional group of interest is a quaternary alkylammonium functional group and the β-carbon is the second carbon from the alkylammonium functional group.

"Anhydrous" refers to compositions, including salts such as fluoride salts, that are substantially free of water. In an embodiment, for example, anhydrous fluoride salts are provided that are characterized by an amount of water less than 1000 parts per million (ppm) and in some embodiments less than 100 parts per million (ppm). In an embodiment, for example, methods of making fluoride ion containing solutions are provided, where a fluoride salt as disclosed herein is provided in an anhydrous form and at least partially dissolved into one or more non-aqueous solutions.

The term "electrochemical cell" refers to devices and/or device components that convert chemical energy into electrical energy or electrical energy into chemical energy. Electrochemical cells have two or more electrodes (e.g., positive and negative electrodes) and an electrolyte, where electrode reactions occurring at the electrode surfaces result in charge transfer processes. Electrochemical cells include, but are not limited to, primary batteries, secondary batteries, electrolysis systems, and capacitors.

"Electrode" refers to an electrical conductor where ions and electrons are exchanged with electrolyte and an outer circuit. "Positive electrode" and "cathode" are used synonymously in the present description and refer to the electrode having the higher electrode potential in an electrochemical cell (i.e. higher than the negative electrode). "Negative electrode" and "anode" are used synonymously in the present description and refer to the electrode having the lower electrode potential in an electrochemical cell (i.e. lower than the positive electrode). Cathodic reduction refers to a gain of electron(s) of a chemical species, and anodic oxidation refers to the loss of electron(s) of a chemical species. Positive electrodes and negative electrodes of the present electrochemical cell may further include a conductive diluent, such as acetylene black, carbon black, powdered graphite, coke, carbon fiber, and metallic powder, and/or may further comprises a binder, such as a polymer binder. Useful binders for positive electrodes in some embodiments comprise a fluoropolymer such as polyvinylidene fluoride (PVDF). Positive and negative electrodes of the present electrochemical cell may be provided in a range of useful configurations and form factors as known in the art of electrochemistry and battery science, including thin electrode designs, such as thin film electrode configurations. Electrodes are manufactured as disclosed herein and as known in the art, including as disclosed in, for example, U.S. Pat. Nos. 4,052,539, 6,306,540, 6,852,446, each incorporated herein by reference. For some embodiments, the electrode is typically fabricated by depositing a slurry of the electrode material, an electrically conductive inert material, the binder, and a liquid carrier on the electrode current collector, and then evaporating the carrier to leave a coherent mass in electrical contact with the current collector.

Aqueous solutions containing F$^-$ are problematic for use as electrolytes in electrochemical applications. For example, as illustrated in FIG. 1, the F$^-$ ion reacts rapidly with water, forming hydrofluoric acid (HF) and the complex ion HF$_2^-$. The formation of HF is undesirable, as it is highly corrosive and extremely toxic. Further, HF$_2^-$ is much less active than F$^-$ in electrochemical applications and, in extreme cases, may even be inactive. HF$_2^-$ is also undesirable because it will evolve H$_2$ at potentials below the cathodic reaction of interest, limiting the useful voltage window in electrochemical applications and potentially causing an failure of the electrochemical cell (e.g., a battery) in which the electrolyte is employed.

To avoid these problems, the use of non-aqueous F$^-$ electrolyte solutions is desirable. However, non-aqueous solutions of F$^-$ have proven difficult to prepare in concentrations high enough to be useful (e.g., greater than or equal to 0.05 M). For example:

Metal fluorides are highly insoluble in non-aqueous solvents, even in the presence of "solubilizing" species, such as crown ethers. See, for example, D. A. Wynn, et al., "The solubility of alkali-metal fluorides in non-aqueous solvents with and without crown ethers, as determined by flame emission spectroscopy," *Talana*, Vol. 31, No. 11 (November 1984), pp. 1036-1040.

Organic fluorides are typically difficult to dry to remove water contamination due to reactivity of the organic cation with F$^-$ under the drying conditions (e.g., through the Hoffman elimination reaction, as illustrated in FIG. 1). See, for example, R. K. Sharma and J. L. Fry, "Instability of anhydrous tetra-n-alkylammonium fluorides," *J. Org. Chem.*, Vol. 48, No. 12 (June 1983), pp. 2112-2114.

In certain cases where anhydrous organic fluoride salts are known, such as tetramethylammonium fluoride (TMAF), these salts are poorly soluble in non-aqueous solvents. See, for example, K. O. Christe, et al., "Syntheses, properties, and structures of anhydrous tetramethylammonium fluoride and its 1:1 adduct with trans-3-amino-2-buteneitrile," *J. Am. Chem. Soc.*, Vol. 112, No. 21 (October 1990).

To address the forgoing problems, embodiments of the present disclosure present lithium-free, fluoride salts that may be prepared in anhydrous form. The molecular structure of these fluoride salts facilitates their ability to be made anhydrous without decomposition. For example, the fluoride salts include one or more fluoride ions and an organic cation (e.g., having a charge center of N, P, S, or O) that does not possess a carbon in the β-position or does not possess a carbon in the β-position having a bound hydrogen.

Further embodiments of the disclosure present high concentration solutions of these fluoride salts in non-aqueous solvents (e.g., greater than or equal to 0.05 M and up to 20 M in certain cases). As discussed in greater detail below, it has been identified that the combination of these fluoride salts with at least one fluorine-containing non-aqueous solvent promotes solubility of the fluoride salts within the non-aqueous solvents. In further embodiments, the solvent may be a mixture of at least one non-aqueous fluorine-containing solvent and at least one non-aqueous, non-fluorine containing solvent.

Additional embodiments of the disclosure present use of these high concentration electrolyte solutions in electrochemical applications such as fluoride-ion batteries, electrochemical double-layer capacitors, and electrochemical fluorination reactions.

Anhydrous Fluoride Salts

The discussion now turns to design considerations of embodiments of the anhydrous fluoride salts. For some applications, the anhydrous fluoride salts are stable in anhydrous form and do not contain lithium. As further discussed below in the Examples, solutions containing embodiments of the anhydrous fluoride salts and one or more non-aqueous solvents exhibit a concentration of fluoride ions dissolved within one or more non-aqueous solvents that is greater than or equal to 0.05 M. In further embodiments, the concentration of fluoride ions dissolved within one or more non-aqueous solvents is up to 20 M. In additional embodiments, the concentration of fluoride ions is selected over the range of 0.05 M to 20 M.

As discussed above with respect to FIG. 1, it is desirable that the anhydrous fluoride salts avoid the formation of HF and HF$_2^-$. In one embodiment this goal may be achieved by fluoride salts including one or more fluoride ions and an organic cation, where the organic cation does not possess a carbon in the β-position having a bound hydrogen, as this bound hydrogen will react upon drying. For example, as illustrated in FIG. 1, the β-carbon is one carbon atom removed from the nitrogen of the quaternary alkylammonium functional group (N—(CH$_3$)$_3$)—$^+$ and will eliminate HF on drying.

In another embodiment, this goal may be achieved by fluoride salts including one or more fluoride ions and an organic cation, where the organic cation does not possess a carbon in the β-position. The cation charge center may be selected from nitrogen (N), phosphorus (P), sulfur (S), or oxygen (O).

Notably, however, it has been observed that the absence of a carbon in the β-position or the absence of a carbon in the β-position having a bound hydrogen may not be sufficient to promote high levels of solubility of the fluoride salt with non-aqueous solvents. For example, consider tetramethylammonium fluoride (TMAF), illustrated below.

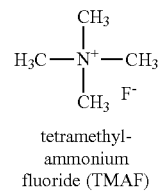

tetramethyl-
ammonium
fluoride (TMAF)

As discussed in detail below, it has been observed that TMAF is not very soluble in non-aqueous solvents.

It has been identified that solubility of fluoride salts that do not contain a carbon in the β-position, or do not possess a carbon in the β-position having a bound hydrogen, may be improved by increasing the degree of alkylation and/or substitution of the cation and/or decreasing the symmetry of the cation. For example, one solution is to substitute the cation with neo-pentyl (2,2-dimethylpropyl) groups, as illustrated in Table 1, therefore avoiding Hofmann elimination upondrying, while increasing solubility through alkylation.

TABLE 1

Substitution of TMAF with neo-pentyl (2,2-dimethylpropyl) groups

| Cation | Hofmann elimination | # of hydrogens bound to β-carbon |
|---|---|---|
| ⌒⌒NMe$_3^{\oplus}$ | Yes | 3 |
| ⌒⌒⌒NMe$_3^{\oplus}$ | Yes | 2 |

TABLE 1-continued

Substitution of TMAF with neo-pentyl (2,2-dimethylpropyl) groups

| Cation | Hofmann elimination | # of hydrogens bound to β-carbon |
|---|---|---|
| 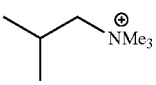 | Yes | 1 |
| 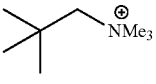 | No | 0 |

As discussed below, neo-pentyl fluoride salts may include, but are not limited to, (2,2-dimethylpropyl)trimethylammonium fluoride ($NpMe_3NF$) and bis(2,2-dimethylpropyl)dimethylammonium fluoride ($Np_2Me_2NF$). In general, embodiments of the anhydrous fluoride salt may be substituted or unsubstituted ammonium fluoride salts.

Without being bound by theory, it is believed that alkylation and/or substitution of the alkylammonium cation with electron-donating or electron-withdrawing modifies the charge on the cation charge center. Furthermore, as discussed in greater detail below with regards to the solvent and the Examples, when solvents including $CH_2$ moieties having a partial positive charge are combined with such salts, solvation of the cation, as well as the fluoride anions, by the solvent may be improved.

Non Aqueous Solvents

Solvent screening performed using $NpMe_3NF$ as the salt are discussed in detail below in Example 3. Suitable non-aqueous solvent embodiments identified from this screening are outlined below. In an embodiment, the non-aqueous solvent includes at least one fluorinated, non-aqueous solvent. In an embodiment, the non-aqueous solvent is characterized by the form $XCH_2YCH_2X$ or $XCH_2CH_2YCH_2CH_2X$ (i.e., $[X—(CH_2)_n—Y]$, where n=1 or 2), where X and Y are polar functional groups (i.e., electron withdrawing groups) having a combined effect to confer a partial positive charge on the $CH_2$ group or groups. For example, Y may be O or S. X may be a functional group including, but not limited to, ethers, esters, acid anhydrides, amines, amides, carbonates, sulfones, sulfonyl esters, phosphites, phosphates, nitriles, nitro, aldehydes, acetates, $SF_5$, or fluorocarbons (e.g., $—CF_3$, $—CF_2CF_3$).

In another embodiment, the non-aqueous solvent is an aromatic solvent including at least one functional group characterized by the form $[X—(CH_2)_n—Y]$, where n=1 or 2 and where X and Y are polar functional groups having a combined effect to confer a partial positive charge on the $CH_2$ group or groups. In another embodiment of the electrolyte solution, Y is O or S and X is a functional group selected from the group including, but not limited to, ethers, esters, acid anhydrides, amines, amides, carbonates, sulfones, sulfonyl esters, phosphites, phosphates, nitriles, nitro, aldehydes, acetates, $SF_5$, or fluorocarbons (e.g., $—CF_3$, $—CF_2CF_3$).

In further embodiments, the non-aqueous solvent is a mixture of a first non-aqueous fluorine-containing solvent and a second non-aqueous, non-fluorine containing solvent. A ratio of amounts of the first solvent and the second solvent is greater than 1:2. For example, a ratio of amounts of the first solvent and the second solvent is selected from the range from 1:20 to 20:1 and, optionally, from 1:2 to 9:1. In another embodiment, the first solvent and the second solvent are each independently a polar solvent.

Electrolyte Solutions Containing Mixtures Of Fluoride Salts

In additional embodiments, electrolyte solutions containing more than one fluoride salt are contemplated. For example, the electrolyte solution may include a first fluoride salt, a second fluoride salt, and one or more non-aqueous solvents. In some embodiment, for example, the first fluoride salt may include one or more fluoride ions and an organic cation, where the organic cation does not possess a carbon in the β-position or does not possess a carbon in the β-position having a bound hydrogen, and the cation charge center is N, P, S, or O. In some embodiment, for example, the second fluoride salt is different than the first fluoride salt and may include one or more fluoride ions and an organic cation, where the cation charge center is N, P, S, or O. In some embodiment, for example, the concentration of said fluoride ions dissolved in the electrolyte solution is greater than or equal to 0.05 M.

Electrochemical Cells

In a further embodiment, an electrochemical cell is provided. Embodiments of the electrochemical cells of the present disclosure, may include, but are not limited to, primary electrochemical cells, secondary fluoride-ion electrochemical cells, batteries, fuel cells, electrolysis systems, and capacitors. The electrochemical cells include a positive electrode (i.e., a cathode), a negative electrode (i.e., an anode), and an electrolyte solution provided between the positive electrode and the negative electrode. The electrolyte solution may include any embodiment discussed herein.

In an embodiment, electrochemical cells operate on the principle of simultaneous oxidation and reduction reactions that involve accommodation and release of anion charge carriers by positive and negative electrodes comprising different anion charge carrier host materials. In these systems, the electrolyte solution provides for transport of anion charge carriers (e.g., fluoride ions) between positive and negative electrodes during discharge and charging of the anionic electrochemical cell. For example, when utilized in electrochemical cells, embodiments of the disclosed electrolyte solutions may provide conductivity of fluoride ions greater than or equal to 0.1 mS/cm at 25° C.

The following electrode half reactions, cells reactions and electrolyte reactions are provided to set forth and describe the fundamental principles by which anionic electrochemical cells of the present disclosure operate.

(i) Electrode Reactions

For the purpose of illustration, assume $A^-$ is the anion charge carrier, $PA_n$ is the positive electrode anion host material, and $NA_m$ is the negative electrode anion host material. In a primary battery, only discharge reactions occur:

At the positive electrode, $A^-$ is released (Eq. I):

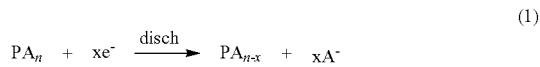

$$PA_n + xe^- \xrightarrow{disch} PA_{n-x} + xA^- \qquad (1)$$

At the negative electrode, $A^-$ is occluded (Eq. 2):

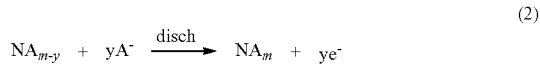

$$NA_{m-y} + yA^- \xrightarrow{disch} NA_m + ye^- \qquad (2)$$

Accordingly, the cell overall reaction is (Eq. 3):

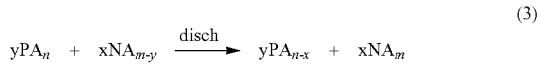

In a secondary battery, Equations 1 and 2 are reversed during charge, therefore the overall cell reaction is (Eq. 4):

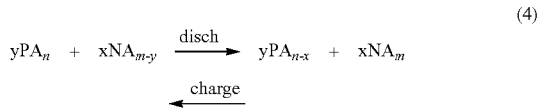

Figure 2:
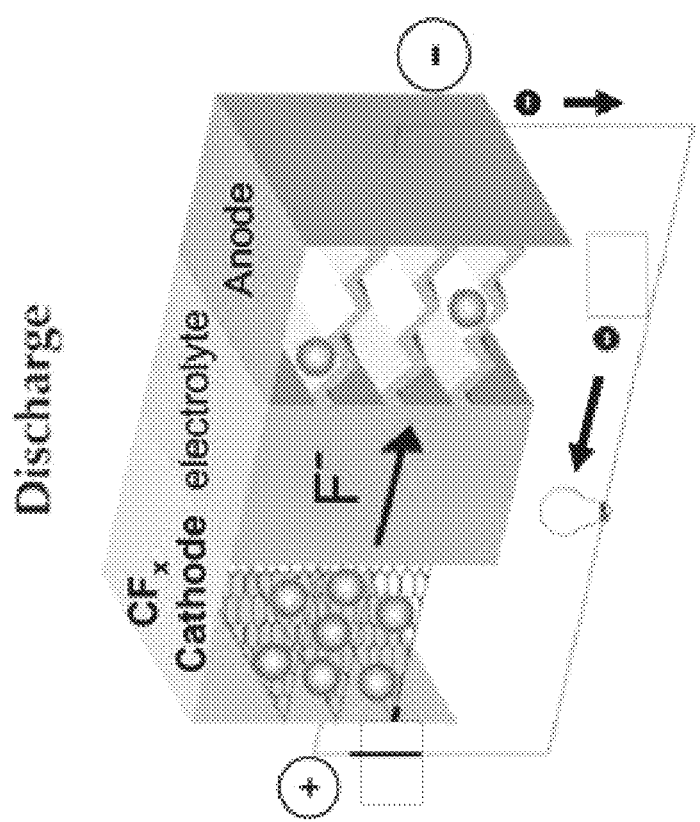
FIG. 2 is a schematic illustration of an embodiment of an electrochemical cell employing embodiments of fluoride-containing electrolytes of the present disclosure.

A schematic illustration of an embodiment of a fluoride ion electrochemical cell during discharge is presented in FIG. 2. During discharge, fluoride anions are released from the positive electrode (i.e., designated cathode), migrate through the electrolyte, and are accommodated by the negative electrode (i.e., designated anode). As shown in FIG. 2, the direction of the flow of electrons during discharge is from the negative electrode to the positive electrode. During charging of a fluoride ion electrochemical cell, fluoride anions are released from the negative electrode migrate through the electrolyte and are accommodated by the positive electrode. The direction of the flow of electrons during charging is from the positive electrode to the negative electrode. Release and accommodation of fluoride ions during discharge and charging results from oxidation and reduction reactions occurring at the electrodes.

A wide range of electrode materials may be used in conjunction with embodiments of the disclosed liquid electrolytes. To improve safety, lithium-free electrodes, or substantially lithium free, or electrodes with low weight percentage lithium (e.g., less than 10% lithium) may be employed.

(ii) Electrode Composition

Active materials for positive and negative electrodes of fluoride ion electrochemical cells of the present disclosure include fluoride ion host materials capable of accommodating fluoride ions from the electrolyte during discharge and charging of the electrochemical cell. In this context, accommodation of fluoride ions includes insertion of fluoride ions into the host material, intercalation of fluoride ions into the host material and/or reaction of fluoride ions with the host material. Accommodation includes alloy formation reactions, surface reaction and/or bulk reactions with the host material. Use of fluoride ion host materials that are capable of reversibly exchanging fluoride ions with the electrolyte without significant degradation of the fluoride ion host material upon cycling is preferred for secondary fluoride ion batteries of the present disclosure.

In an embodiment, a negative electrode of a fluoride ion electrochemical cell of the present disclosure comprises a fluoride ion host material, such as a fluoride compound, having a low standard reduction potential, preferably less than or equal to about −1V for some applications, and more preferably less than or equal to about −2 V for some applications. Useful fluoride ion host materials for negative electrodes of electrochemical cells include, but are not limited to: $LaF_x$, $CaF_x$, $AlF_x$, $EuF_x$, $LiC_6$, $Li_xSi$, $Li_xGe$, $Li_x(CoTiSn)$, $SnF_x$, $InF_x$, $VF_x$, $CdF_x$, $CrF_x$, $FeF_x$, $ZnF_x$, $GaF_x$, $TiF_x$, $NbF_x$, $MnF_x$, $YbF_x$, $ZrF_x$, $SmF_x$, $LaF_x$ and $CeF_x$. Preferred fluoride host materials for negative electrodes of electrochemical cell are element fluorides $MF_x$, where M is an alkali-earth metal (Mg, Ca, Ba), M is a transition metal, M belongs to column 13 group (B, Al, Ga, In, Tl), or M is a rare-earth element (atomic number Z between 57 and 71). The present disclosure also includes negative electrode fluoride ion host materials comprising a polymer(s) capable of reversibly exchanging fluoride ions comprising the anion ion charge carriers. Examples of such a conjugated polymers are, but not limited to: polyacetylene, polyaniline, polypyrrol, polythiophene and polyparaphenylene. Polymer materials useful for negative electrodes in the present disclosure are further set forth and described in Manecke, G. and Strock, W., in "Encyclopedia of Polymer Science and Engineering, $2^{nd}$ Edition," Kroschwitz, J., I., Editor. John Wiley, New York, 1986, vol. 5, pp. 725-755, which is hereby incorporated by reference to the extent not inconsistent with the disclosure herein.

In an embodiment, a positive electrode of a fluoride ion electrochemical cell of the present disclosure comprises a fluoride ion host material, such as a fluoride compound, having a high standard reduction potential, preferably for some applications greater than or equal to about 1V, and more preferably for some applications greater than or equal to about 2 V. In an embodiment, the fluoride ion host material of the positive electrode is an intercalation host material capable of accommodating fluoride ions so as to generate a fluoride ion intercalation compound. "Intercalation" refers to the process where an ion inserts into a host material to generate an intercalation compound via a host/guest solid state redox reaction involving electrochemical charge transfer processes coupled with insertion of mobile guest ions, such as fluoride ions. Major structural features of the host material are preserved after insertion of the guest ions via intercalation. In some host materials, intercalation refers to a process where guest ions are taken up with interlayer gaps (e.g., galleries) of a layered host material.

Useful fluoride ion host materials for positive electrodes of electrochemical cells of the present disclosure include, but are not limited to, $CF_x$, $AgF_x$, $CuF_x$, $NiF_x$, $CoF_x$, $PbF_x$, $CeF_x$, $MnF_x$, $AuF_x$, $PtF_x$, $RhF_x$, $VF_x$, $OsF_x$, $RuF_x$, and $FeF_x$. In an embodiment, the fluoride ion host material of the positive electrode is a subfluorinated carbonaceous material having a formula $CF_x$, where x is the average atomic ratio of fluorine atoms to carbon atoms and is selected from the range of about 0.3 to about 1.0. Carbonaceous materials useful for positive electrodes of this embodiment are selected from the group consisting of graphite, graphene, coke, single or multi-walled carbon nanotubes, multi-layered carbon nanofibers, multi-layered carbon nanoparticles, carbon nanowhiskers and carbon nanorods. The present disclosure also includes positive electrode fluoride ion host materials comprising a polymer(s) capable of reversibly exchanging fluoride ions comprising the anion ion charge carriers. Examples of conjugated polymers for positive electrodes include, but not limited to: polyacetylene, polyaniline, polypyrrol, polythiophene and polyparaphenylene.

EXAMPLES

The following specific examples are given to illustrate the practice of embodiments of the disclosed anhydrous fluoride salts, electrolyte solutions, and electrochemical cells but are not to be considered as limiting in any way.

Example 1—Synthesis and Characterization of Anhydrous Neo-Pentyl Ammonium Fluoride Salts Improved methods for synthesizing 10 gram-scale batches of two neo-pentyl ammonium fluoride anhydrous salts, (2,2-dimethylpropyl)trimethylammonium fluoride (NpMe$_3$NF) and bis(2,2-dimethylpropyl)dimethylammonium fluoride (Np$_2$Me$_2$NF), are discussed below.

(i) NpMe$_3$NF:

NpMe$_3$NF is formed from a neo-pentylamine starting material (C$_5$H$_{13}$N) and the net reaction illustrated below (E1-1):

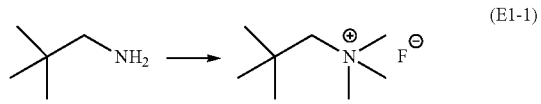
(E1-1)

For example the neo-pentylamine is treated with formic acid and formaldehyde to form N,N,2,2-tetramethyl-1-propanamine (E1-1a):

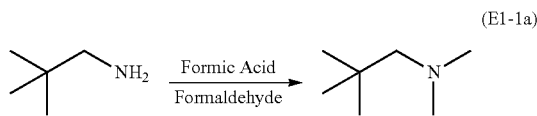
(E1-1a)

Subsequently, N,N,2,2-tetramethyl-1-propanamine is methylated by treatment with CH$_3$I to form the ammonium salt NpMe$_3$NI (E1-1b):

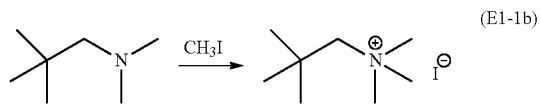
(E1-1b)

Alternatively, the neo-pentylamine may be exhaustively methylated by treatment with excess CH$_3$I, with K$_2$CO$_3$ and EtOH, followed by recrystallization from 2-propanol, to directly yield the ammonium salt NpMe$_3$NI (E1-1a'):

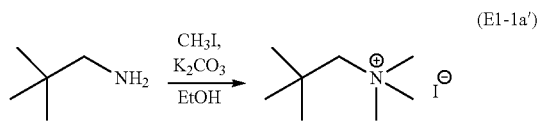
(E1-1a')

This latter synthesis route greatly reduces the reaction time and improves overall yield.

Subsequently, the iodine anion is replaced by a hydroxyl anion by reaction with Ag$_2$O and H$_2$O (E1-1c):

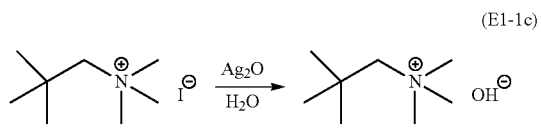
(E1-1c)

This reaction is run for one hour, then filtered and the filtrate used directly in the next reaction (E1-1d).

Finally, an HF titration procedure is followed to yield NpMe$_3$NF (E1-1d):

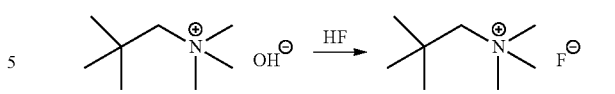
(E1-1d)

An azeotropic drying process was used, removing a majority of the water from the mixture using "benchtop" (i.e., not anhydrous) 2-propanol solvent on a rotary evaporator (3x). Subsequently, the mixture is filtered in a 2-propanol solution through a micron filter (0.2 μm) to remove a trace of gray impurity (presumably residual silver salt). After filtration, anhydrous 2-propanol is used to dry the remaining material by 5x azeotropic water removal. The resulting white powder is dried at 100° C. at about 80 mTorr for 5 days. To ensure purity and complete removal of trace amounts of water, the white powder was thoroughly crushed with a dry mortar and pestle in a glove box under an argon atmosphere. The finely crushed powder was transferred to a dry plastic bottle and then placed at about 80 mTorr for 7 days. The total yield of anhydrous NpMe$_3$NF is about 10g (88% from the iodide).

(ii) Np$_2$Me$_2$NF:

Np$_2$Me$_2$NF is formed from the neo-pentylamine starting material (C$_5$H$_{13}$N) and the net reaction is illustrated below (E1-2):

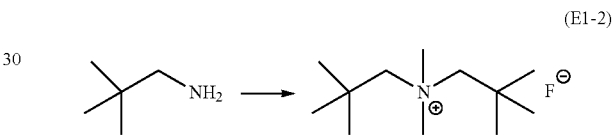
(E1-2)

For example the neo-pentylamine is treated with trimethylacetyl chloride, chloroform (CHCl$_3$) and triethanolamine (TEA) to form N-neopentyl pivalamide (E2-2a):

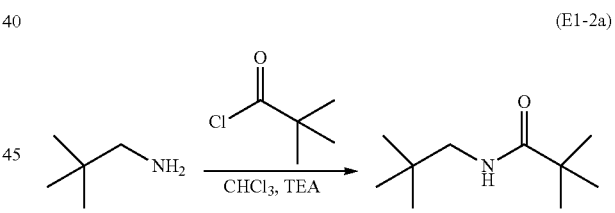
(E1-2a)

Subsequently, N-neopentyl pivalamide is treated with lithium aluminum hydride (LiAlH$_4$), n-butyl ether (n-Bu ether), and diethyl ether to form the secondary amine di-neopentyl amine (E1-2b):

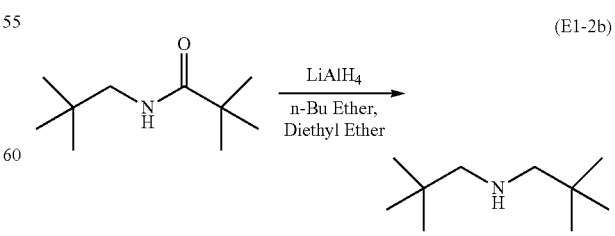
(E1-2b)

Methylation of di-neopentyl amine is performed for 6 days under reflux in acetonitrile to form the ammonium salt Np$_2$Me$_2$NI (E1-2c):

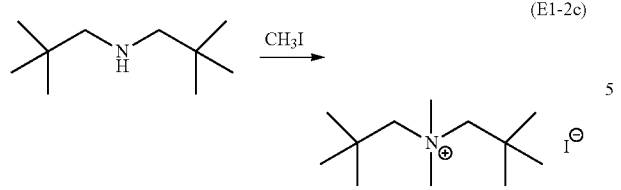

(E1-2c)

The modified post-titration drying procedure described above is also followed here to convert the $Np_2Me_2NI$ to $Np_2Me_2NF$ (E1-2d), (E1-2e):

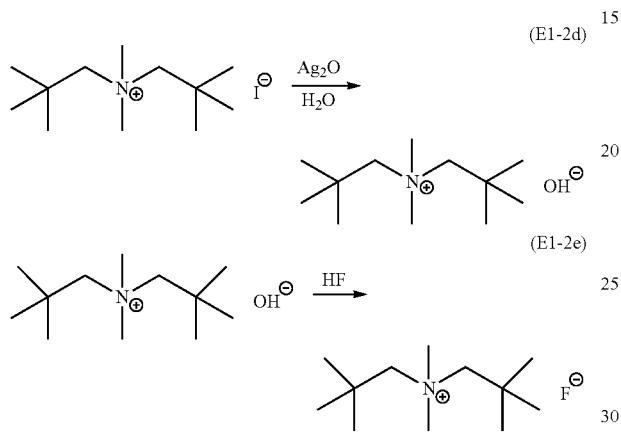

The total yield of anhydrous $Np_2Me_2NF$ is about 10g, with 87% from the iodide.

Figure 3A:
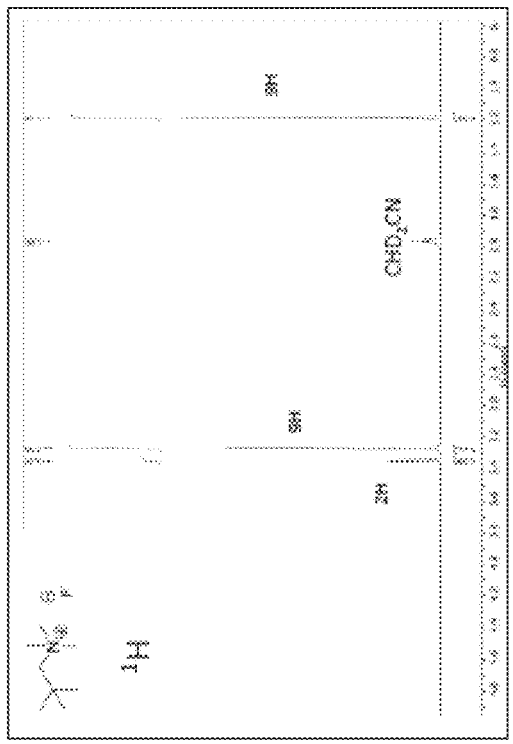
FIGS. 3A-3B are $^1$H and $^{19}$F NMR spectra of the product of an embodiment of a proposed synthesis route for preparation of (2,2-dimethylpropyl)trimethylammonium fluoride (NpMe$_3$NF)
Figure 3B:
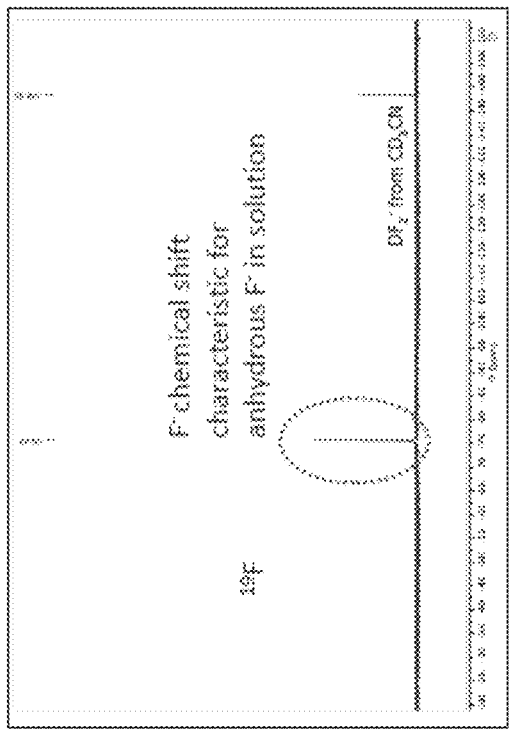

(iii) NMR Characterization:

The synthesized $NpMe_3NF$ and $Np_2Me_2NF$ salts are characterized by $^1H$ and $^{19}F$ NMR spectroscopy, respectively, in deuterated acetonitrile (CD3CN). The measured NMR spectra for $NpMe_3NF$ are illustrated in FIGS. 3A-3B. The measured NMR spectra for $Np_2Me_2NF$ are illustrated in FIGS. 4A-4B.

Figure 4A:
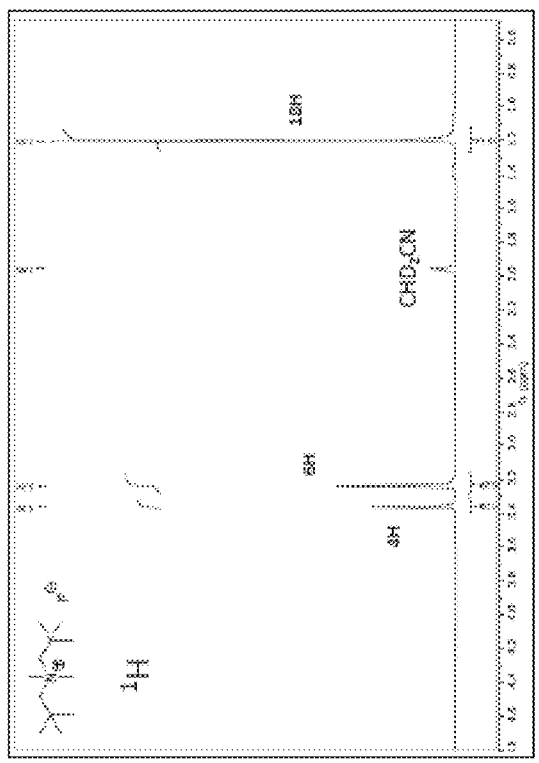
FIGS. 4A-4B are $^1$H and $^{19}$F NMR spectra of the product of an embodiment of a proposed synthesis route for preparation of and bis(2,2-dimethylpropyl)dimethylammonium fluoride (Np$_2$Me$_2$NF)
Figure 4B:
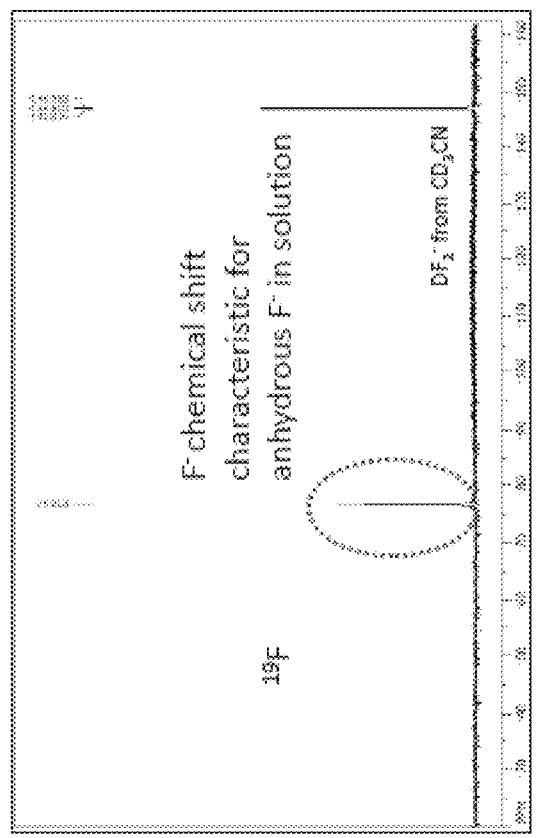
Figures 5A, 5B:
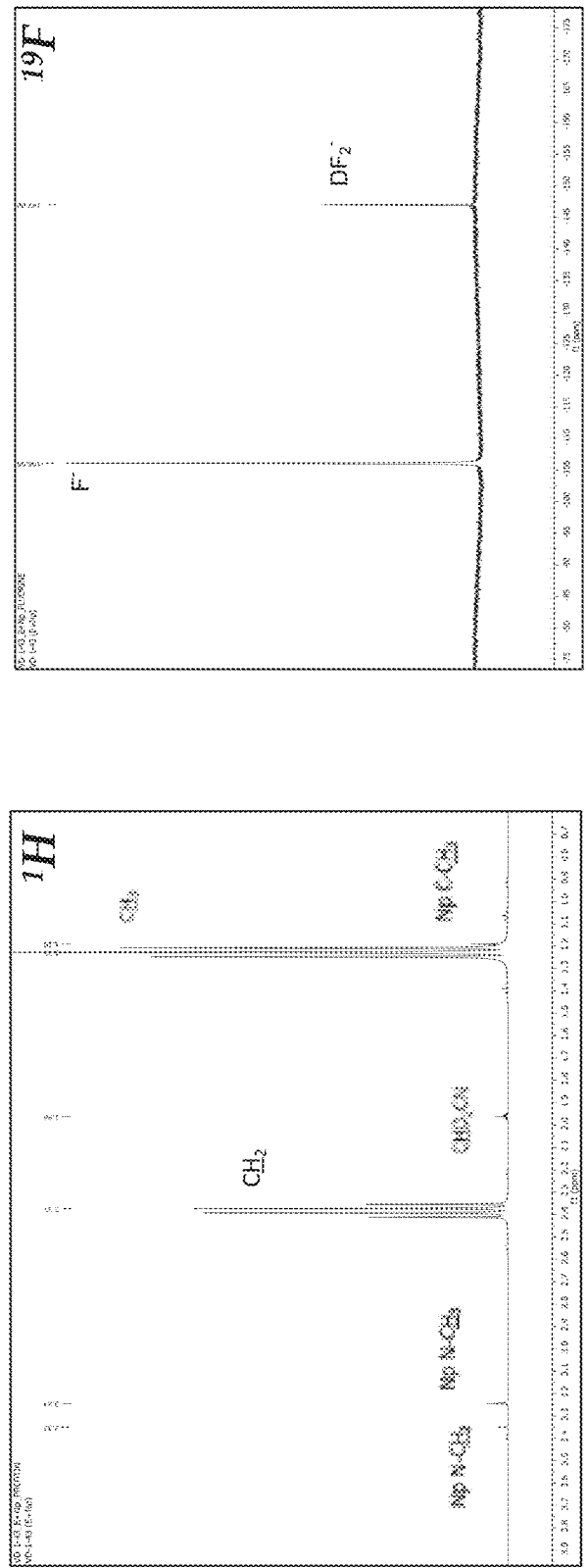
FIGS. 5A-5B are $^1$H and $^{19}$F NMR spectra of a solution of NpMe$_3$NF and propionitrile (PN)
Figure 8A:
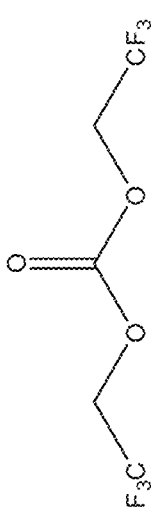
FIGS. 8A-8B are $^1$H and $^{19}$F NMR spectra of a solution of NpMe$_3$NF and Bis(2,2,2-trifluoroethyl) carbonate (BTFEC)
Figure 8A:
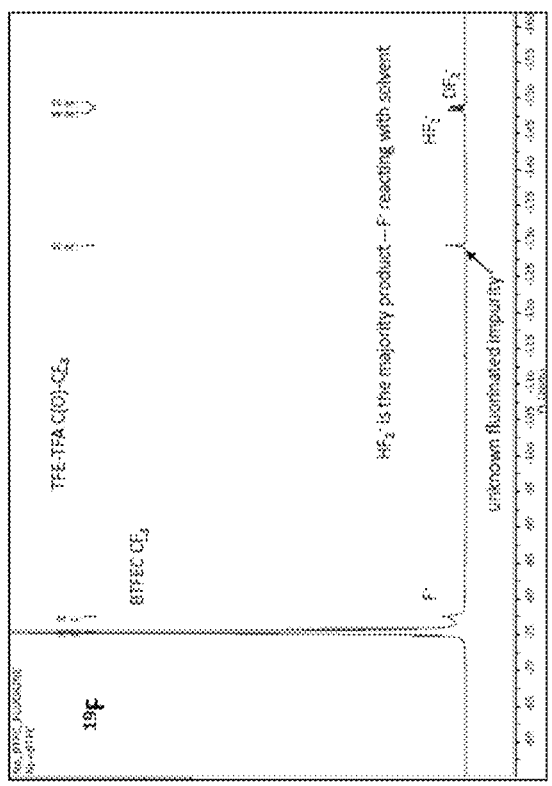
Figure 8B:
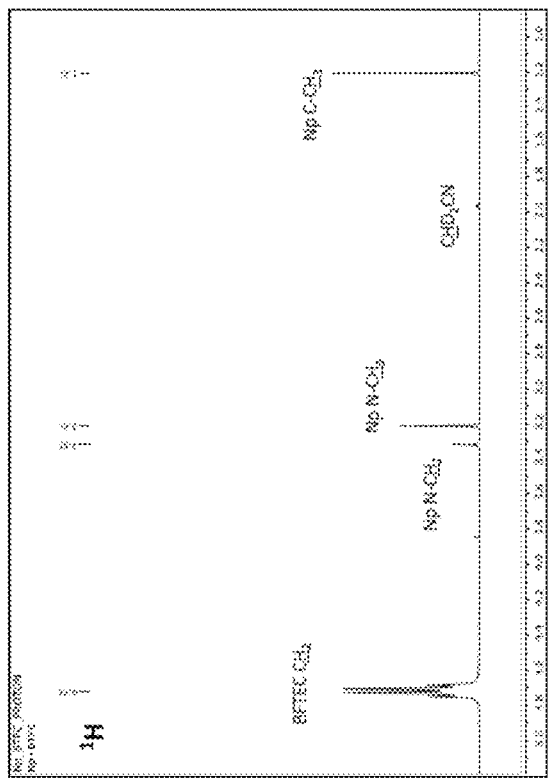
Figure 9B:
FIGS. 9A-9B are $^1$H and $^{19}$F NMR spectra of a solution of NpMe$_3$NF and 3-methoxypropionitrile (3-MeOPN)
Figure 9B:
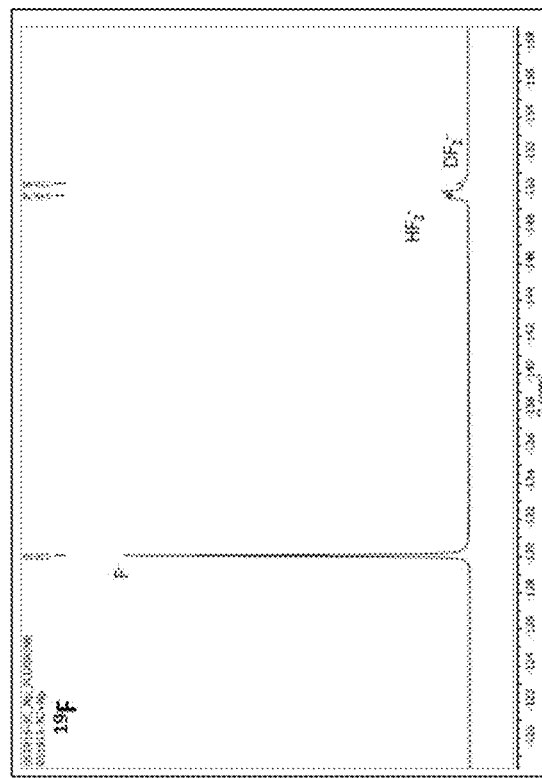
Figure 9A:
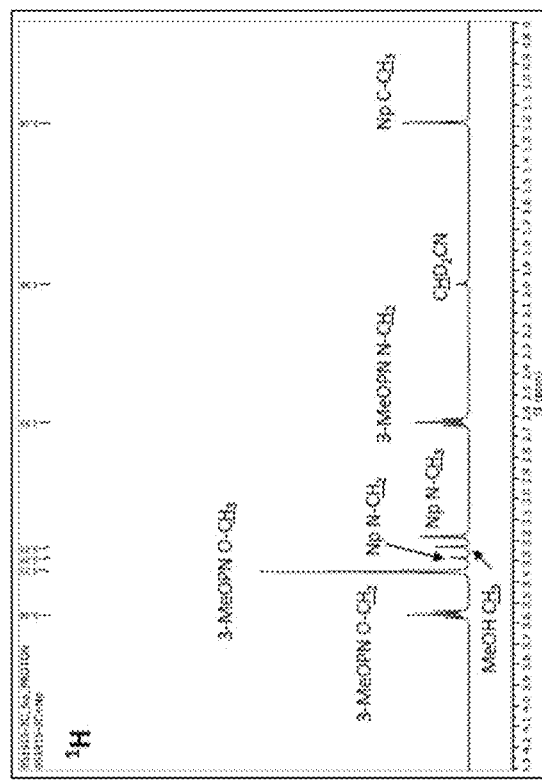

With reference to the $^1H$ spectra illustrated in FIGS. 3A, 4A, it is observed that the synthesized $NpMe_3NF$ and $Np_2Me_2NF$ salts are free from major impurities With reference to the $^{19}F$ spectra illustrated in FIGS. 3B, 4B, the $F^-$ chemical shift characteristic for anhydrous $F^-$ in CD3CN solution is observed in each case.

Example 2—Solvent Screening Using $NpMe_3NF$

Solubility and stability of $NpMe_3NF$ in various solvent classes is screened and the results are presented below in Table 2. $NpMe_3NF$ is determined to be soluble in a given solvent if the concentration of $NpMe_3NF$ dissolved within the solvent is greater than 0.05 M.

(i) $NpMe_3NF$ Solubility:

TABLE 2

| Solubility of $NpMe_3NF$ in various non-aqueous solvents | |
|---|---|
| Solvent | Approximate Solubility (Mol/L) |
| bis(2,2,2-trifluoroethyl)ether (BTFE) | 19.31 |
| Tris(2,2,2-trifluoroethyl)phosphite (TTFP) | 1.05 |
| 2,2,2-trifluoroethyl trifluoroacetate (TFE-TFA) | 0.95 |
| methoxyacetonitrile (MeOAN) | 0.80 |
| 3-methoxypropionitrile (3-MeOPN) | 0.78 |
| Fluoroethylene carbonate (FEC) | 0.71 |
| phenyl trifluoroacetate (PhTFA) | 0.47 |
| 2,3-difluorobenzonitrile (2,3-$F_2$BN) | 0.40 |
| 2,6-difluoropyridine (2,6-$F_2$Py) | 0.39 |
| 3-fluorobenzonitrile (3-FBN) | 0.19 |

TABLE 2-continued

Solubility of NpMe₃NF in various non-aqueous solvents

| Solvent | Approximate Solubility (Mol/L) |
|---|---|
| (Dimethylamino)acetonitrile (DMAN) | 0.14 |
| 2-fluorobenzonitrile (2-FBN) | 0.12 |
| 1,3-Dimethyl-3,4,5,6-tetrahydro-2(1H)-pyrimidinone (DMPU) | 0.11 |
| Propionitrile (PN) | 0.07 |

On review of the results of Table 2, it is observed that the solvents providing the highest NpMe₃NF solubility are fluorinated solvents (i.e., BTFE, TTFP, TFE-TFA). Furthermore, the solubility of NpMe₃NF BTFE is very large. Approximately 0.195g NpMe₃NF (1.3 mmol) is found to dissolve in 0.95g BTFE (0.068 mL), indicating that NpMe₃NF has an approximate solubility in BTFE above 19M (19.31M). Furthermore, the solubility of NpMe₃NF in BTFE is significantly higher than that of the other solvents examined.

(ii) Solubility Comparison: TMAF vs. NpMe₃NF and Np₂Me₂NF

Further comparisons between the solubility of TMAF, NpMe₃NF, and Np₂Me₂NF are performed using the fluorinated solvents 3-fluorobenzonitrile and BTFE, illustrated in Tables 3 and 4.

TABLE 3

Solubility of TMAF, NpMe₃NF, and Np₂Me₂NF in 3-fluorobenzonitrile

| Salt | Structure | Solubility in 3-fluorobenzonitrile | Solubility vs. TMAF |
|---|---|---|---|
| TMAF | (structure) | 0.03M | |
| NpMe₃NF | (structure) | 0.19M | >6× |
| Np₂Me₂NF | (structure) | 0.34M | >10× |

TABLE 4

Solubility of TMAF and NpMe₃NF in BTFE

| Salt | Solubility in BTFE |
|---|---|
| TMAF | trace |
| NpMe₃NF | 19.3M |

It is observed that TMAF is not soluble in these fluorinated solvents at useful concentrations (e.g., >0.05 M). In contrast, NpMe₃NF and Np₂Me₂NF exhibit significantly higher solubility. These results indicate that the combination of a fluoride salt with a fluoride-containing cation and fluorinated solvents is needed to obtain high solubility in non-aqueous solvents.

(iii) NpMe₃NF Stability:

NpMe₃NF stability in various solvents is analyzed by $^1$H and $^{19}$F NMR measurements. Preliminary criteria used for a solvent being "chemically stable" to the F⁻ ion are observation of a clear, sharp peak in the $^{19}$F spectrum, alongside a 1:1:1 triplet arising from the $DF_2^-$ formation from the deuterated acetonitrile solvent (CD3CN). The corresponding $^1$H and $^{19}$F NMR spectra are illustrated in FIGS. 5-9. It is observed that propionitrile (PN), BTFE, and 2,6-difluoropyridine (2,6-F₂Py), exhibited good stability. In contrast, for example, Bis(2,2,2-trifluoroethyl) carbonate (BTFEC) and 3-methoxypropionitrile (3-MeOPN) exhibited poor stability.

Example 3—Theoretical Modeling of Fluoride-Solvent Interaction

Theoretical modeling is performed to better understand the nature of the interaction between the above-identified quaternary alkylammonium fluoride salts and solvents giving rise to enhanced solubility. Fluoride salts TMAF, NpMe₃NF, and Np₂Me₂NF and a range of substituted alkyl- and benzylammonium salts in BTFE, glymes, and related solvents are investigated.

Figure 10:
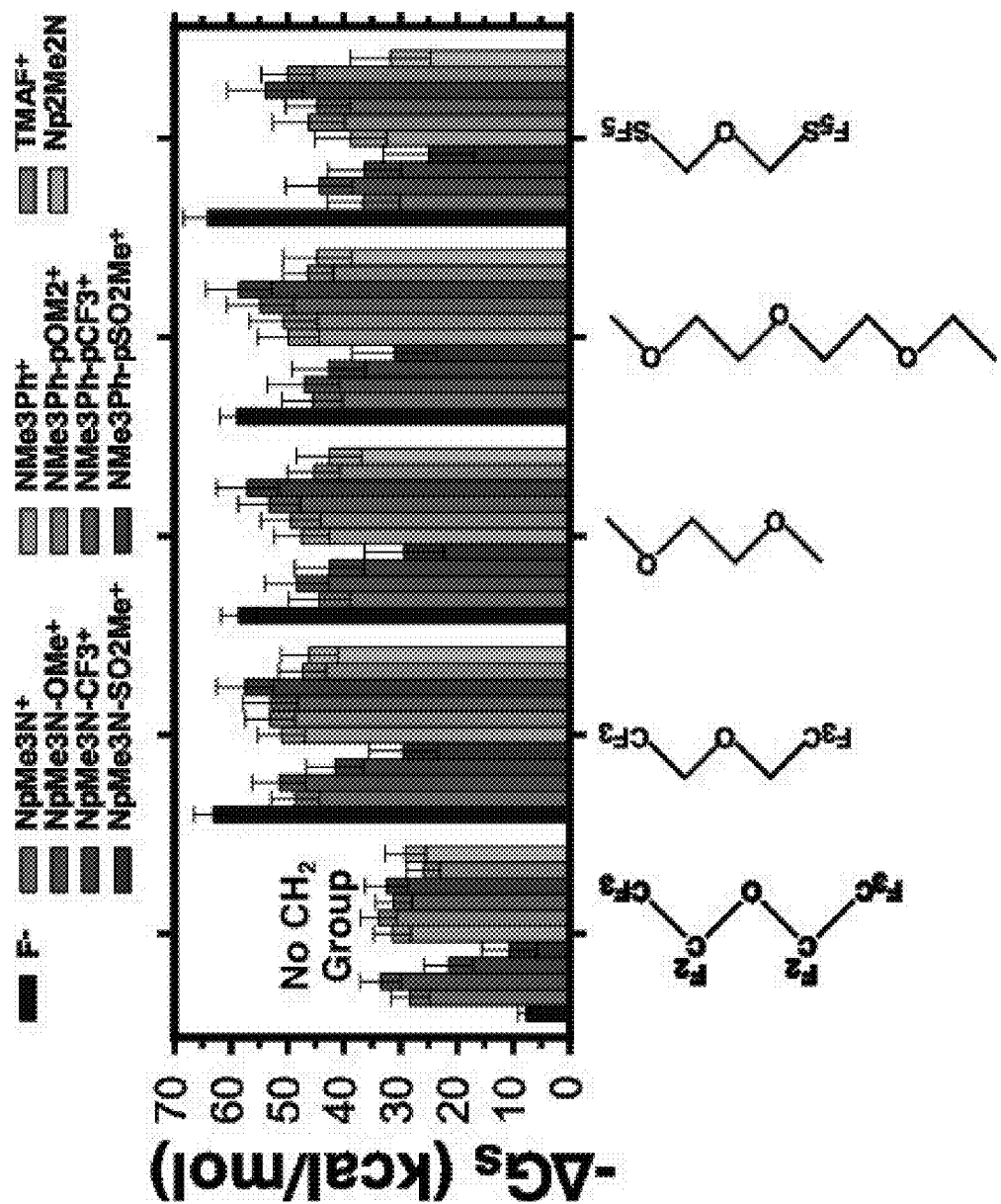
FIG. 10 is a plot of calculated solvation free energy ($\Delta G_s$) for fluoride ion and different cations in solvents with and without a positively polarized CH$_2$ moiety.

(i) Solvation Free Energy:

Calculated solvation free energies ($\Delta G_s$) for fluoride and several cations in solvents (i) without a positively polarized $CH_2$ moiety in the solvent (leftmost solvents) and (ii) solvents with a positively polarized $CH_2$ moiety in the solvent (i.e., characterized by the form [X—(CH₂)ₙ—Y], where n=1 or 2) are shown in FIG. 10. The solvation free energy is calculated as a transfer free energy from vacuum into the solvent using the thermodynamic integration method.

With reference to the solvent that does not include a $CH_2$ moiety, removal of $CH_2$ moiety is observed to result in a tremendous decrease in fluoride salt solubility. Conversely, solvents characterized by the form X—CH₂—Y—CH₂—X and X—CH₂CH₂—Y—CH₂CH₂—X exhibit up to a tenfold increase in the calculated fluoride solvation free energy. These simulations illustrate that the relative increase in fluoride solvation due to the fluoride:$CH_2$ interaction and how this may be modulated by appropriate substitution in the cation molecular structure.

Figure 11B:
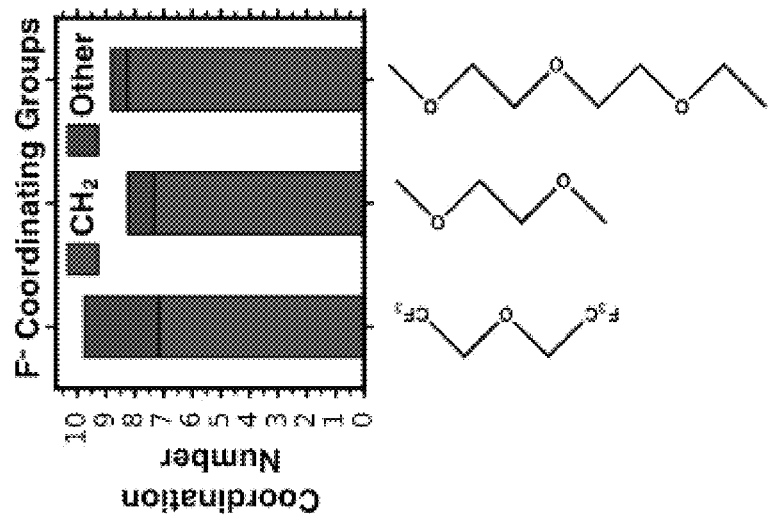
FIG. 11B is a plot of fluoride ion coordination number as a function of solvent for BTFE, 1,2-dimethoxyethane, and 1-ethoxy-2-(methoxyethoxy)ethane.
Figure 11A:
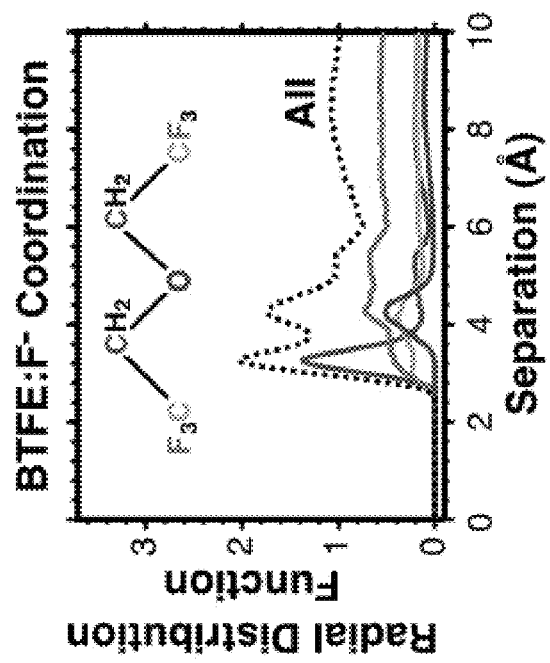
FIG. 11A is a plot of radial distribution function as a function of separation for fluoride ions in a BTFE solvent at dilute concentration.
Figure 12:
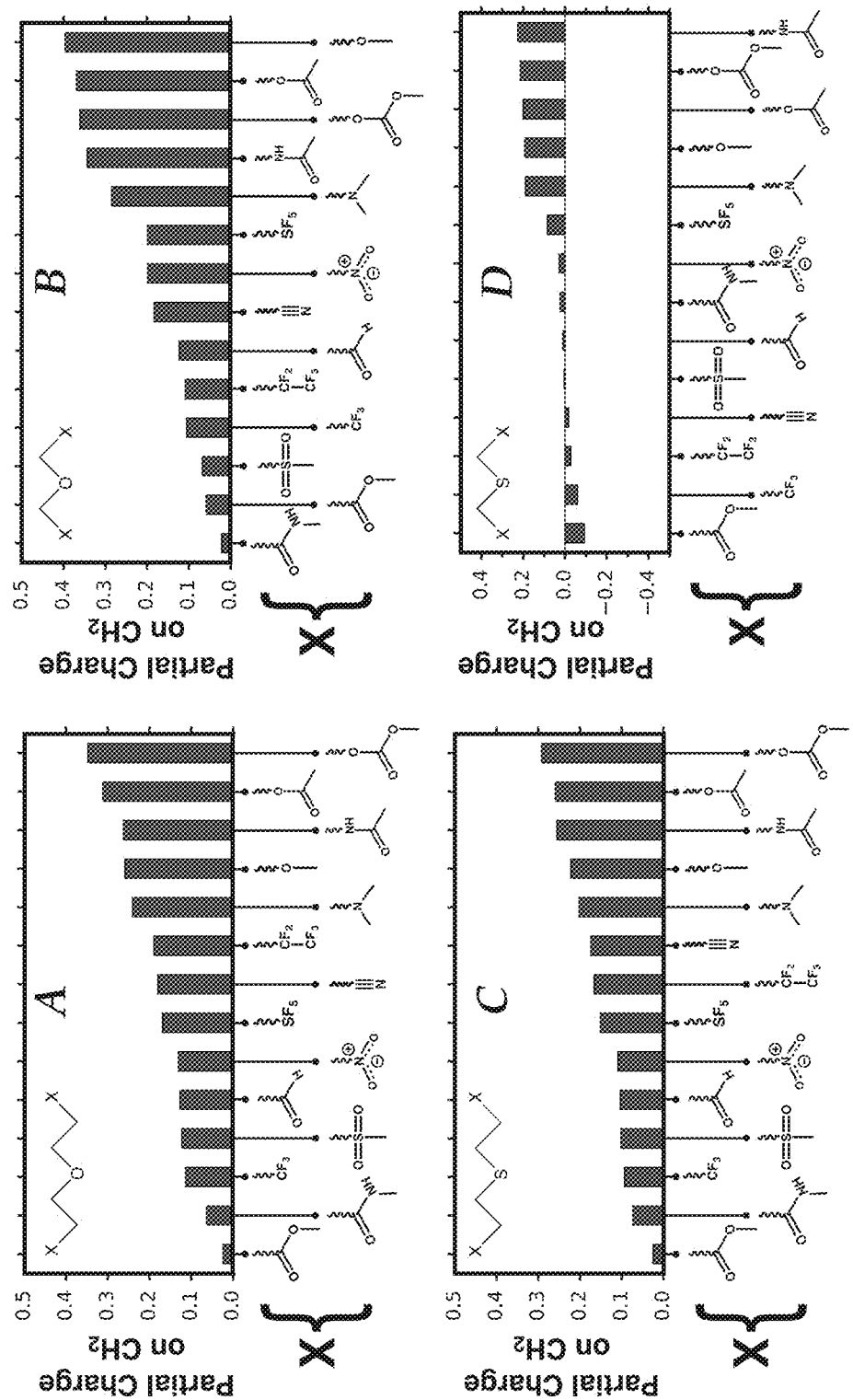
FIGS. 12, A-D are plots of partial charge on CH$_2$ in various solvent molecules characterized by the form X—CH$_2$—Y—CH$_2$—X and X—CH$_2$—CH$_2$—Y—CH$_2$—CH$_2$—X.

(ii) Molecular Dynamics Simulations:

Molecular dynamics simulations of fluoride in a range of solvents are performed to determine statistically averaged fluoride coordination structures, as shown in FIGS. 11A-11B. With reference to FIG. 11A, the radial distribution function for BTFE:$F^-$ coordination shows which groups are present at various displacements from the fluoride and demonstrates the majority presence of $CH_2$ in the first coordination shell.

With reference to FIG. 11B, simulation results calculating the average number of non-hydrogen atoms in the first fluoride coordination shell in several solvents (BTFE, 1,2-dimethoxyethane, and 1-ethoxy-2-(methoxyethoxy)ethane) are presented. Examining the structure of BTFE, it may be observed that each $CH_2$ group is adjacent one oxygen and one $CF_3$ group. In contrast, in both 1,2-dimethoxyethane and 1-ethoxy-2-(methoxyethoxy)ethane, the $CH_2$ group is adjacent two oxygens, with the 1-ethoxy-2-(methoxyethoxy)ethane possessing an additional oxygen and two additional methylene adjacent thereto, as compared to 1,2-dimethoxyethane. In general, both the $CF_3$ group and oxygen are electron-withdrawing, In the case of each solvent, there is a significant preferential association of fluoride with $CH_2$, as compared to other functional groups, as evidenced by the coordination number of $CH_2$ (~7-8) being higher than that that for all other functional groups combined (~1-3). This observation supports the proposition that association of fluoride with $CH_2$ is promoted by the presence of electron-withdrawing groups adjacent the $CH_2$ groups. This observation further allows for rational choice of the solvent or solvent mixture to improved fluoride salt solubility.

(iii) Partial Charge Analysis:

Partial atomic charges on $CH_2$ groups are further investigated for solvent molecules characterized by the form X—$CH_2$—Y—$CH_2$—X and X—$CH_2$—$CH_2$—Y—$CH_2$—$CH_2$—X, where X and Y are electron withdrawing groups having a combined effect to confer a partial positive charge on the $CH_2$ group or groups, to explore this hypothesis. Y is O or S and X is a functional group selected from ethers, esters, acid anhydrides, amines, amides, carbonates, sulfones, sulfonyl esters, phosphites, phosphates, nitriles, nitro, aldehydes, acetates, $SF_5$, or fluorocarbons (e.g., —$CF_3$, —$CF_2CF_3$). The partial charges are calculated using the CHELP algorithm with density functional theory calculated electron densities (B3LYP/def2-PVTZ level of theory) and are illustrated in FIGS. 12A-12D.

It is observed that, solvent molecules characterized by the form X—$CH_2$—Y—$CH_2$—X and X—$CH_2$—$CH_2$—Y—$CH_2$—$CH_2$—X consistently exhibit increased positive charge on the $CH_2$ moieties. In conjunction with the above theoretical results, this demonstrates that positively charged $CH_2$ groups mediate fluoride coordination and dissolution in a particular solvent or solvent mixture across a wide variety of electron withdrawing units.

Example 4—Electrochemical Testing of $NpMe_3NF$ and $Np_2Me_2NF$ Solutions (i) Baseline Electrochemical Testing of $NpMe_3NF$ Solutions Ionic conductivities for a number of anhydrous $NpMe_3NF$ and $Np_2Me_2NF$ solutions are investigated at 0, 10, 25 and 40° C. by AC impedance spectroscopy. Measurements are acquired between 100 mHz and 1 MHz using an air-free glass conductivity cell including a Teflon ring sealing the solution between two parallel Pt electrodes. The Pt electrodes are separated by ~1 cm (the cell constant is determined before each experiment by measuring the conductivity of 0.1M KCl (aq.)). Thermal control is provided by a Tenney TUJR chamber, with the sample allowed to reach thermal equilibrium before measurement (as determined by observation of no change in the impedance spectrum over time).

Figure 13:
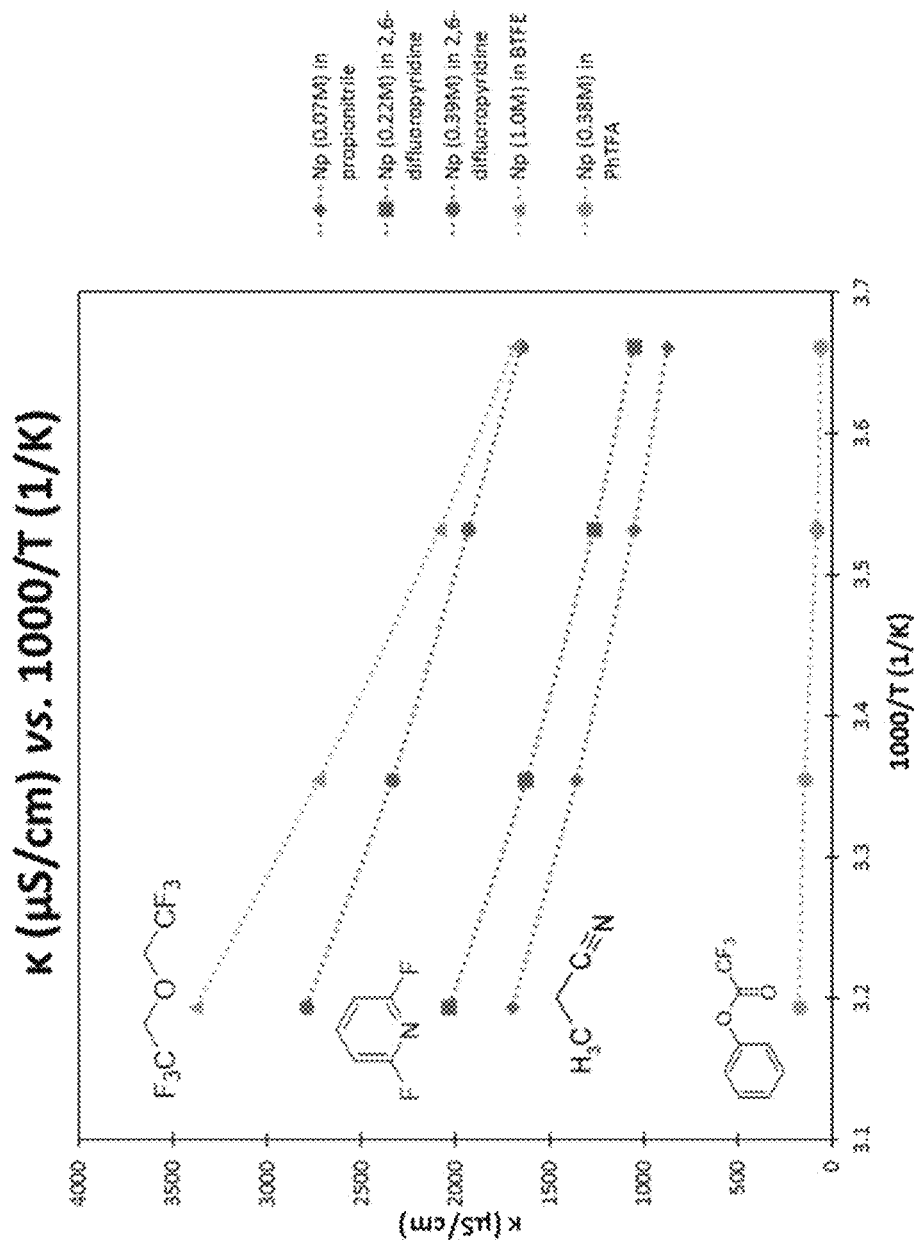
FIG. 13 is a plot of temperature-dependent ionic conductivities for anhydrous solutions of NpMe$_3$NF in PN, 2,6-F$_2$Py, BTFE, and PhTFA between 0-40° C. Water contents of these solutions measured by Karl Fisher titration after the experiments are 42 ppm (BTFE), 4 ppm (2,6-difluoropyridine), and 137 ppm (propionitrile)
Figure 14:
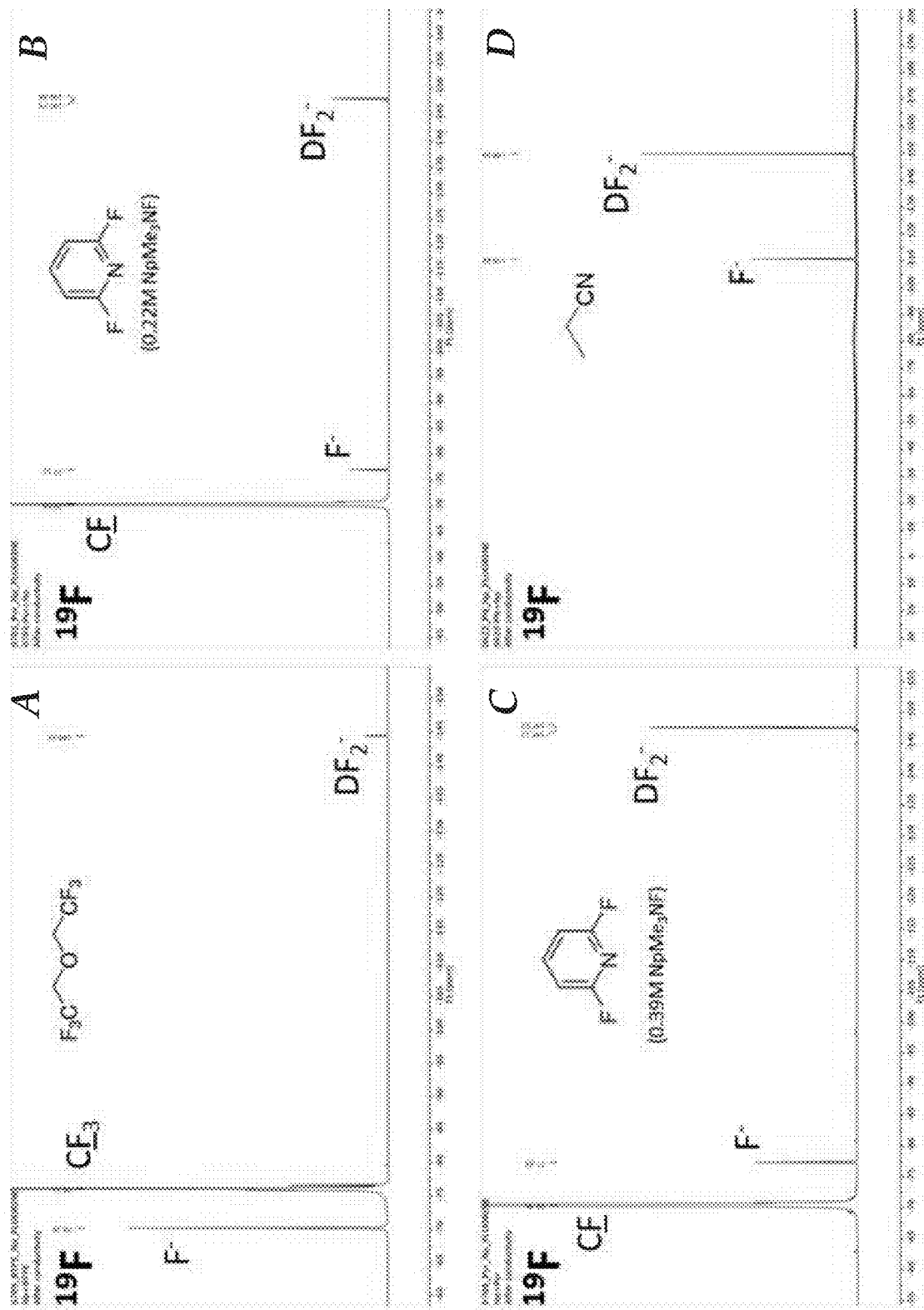
FIGS. 14, A-D are $^{19}$F NMR spectra of the BTFE, 2,6-F$_2$Py and PN solutions after conductivity experiments.

FIG. 13 presents the ionic conductivity measurements for $NpMe_3NF$ (0.07 M) in PN, $NpMe_3NF$ (0.22 M) in 2,6-$F_2Py$, $NpMe_3NF$ (0.35 M) in 2,6-$F_2Py$, $NpMe_3NF$ (1.0 M) in BTFE, and $NpMe_3NF$ (0.38 M) in PhTFA. Water contents of these solutions measured by Karl Fisher titration after the experiments are 42 ppm (BTFE), 4 ppm (2,6-difluoropyridine), and 137 ppm (propionitrile). These measurements indicate that all solutions exhibit appreciable ionic conductivity (>0.1 mS/cm) at room temperature (25° C.). From these observations, it may be concluded that $NpMe_3NF$ forms mobile $NpMe_3N^+$ and $F^-$ ions upon dissolution in these solvents. In particular, 1 M $NpMe_3NF$ in BTFE displays a room temperature conductivity of 2.7 mS/cm at 25° C., a value that should be high enough for preliminary battery testing, with the option to increase this if necessary through increasing the salt molarity.

All solutions investigated by conductivity appeared stable over the time period of the experiment (3-4 days). For confirmation, $^{19}F$ NMR spectra of the BTFE, 2,6-difluoropyridine, and propionitrile solutions measured after conductivity experiments are presented FIGS. 14A-14D. Hence, it is believed all of these solvents are chemically stable in the presence of dissolved $F^-$ up to at least 40° C. on this timescale.

(ii) Electrochemical Testing of $NpMe_3NF$ and $Np_2Me_2NF$ Solutions

In view of the promising baseline ionic conductivity studies discussed above, further measurements of ionic conductivity of $NpMe_3NF$ and $Np_2Me_2NF$ are performed in BTFE and mixtures of BTFE and PN. Investigations are carried out by AC impedance spectroscopy (measuring between 100 mHz and 1 MHz), using an air-free glass conductivity cell consisting of a Teflon ring sealing the solution between two parallel Pt electrodes separated by ~1 cm (cell constant is determined before each experiment by measuring the conductivity of 0.1 M KCl (aq.)). Thermal control is provided by a Tenney TUJR chamber, with the sample allowed to reach thermal equilibrium before measurement (as determined by observation of no change in the impedance spectrum over time).

Figure 15:
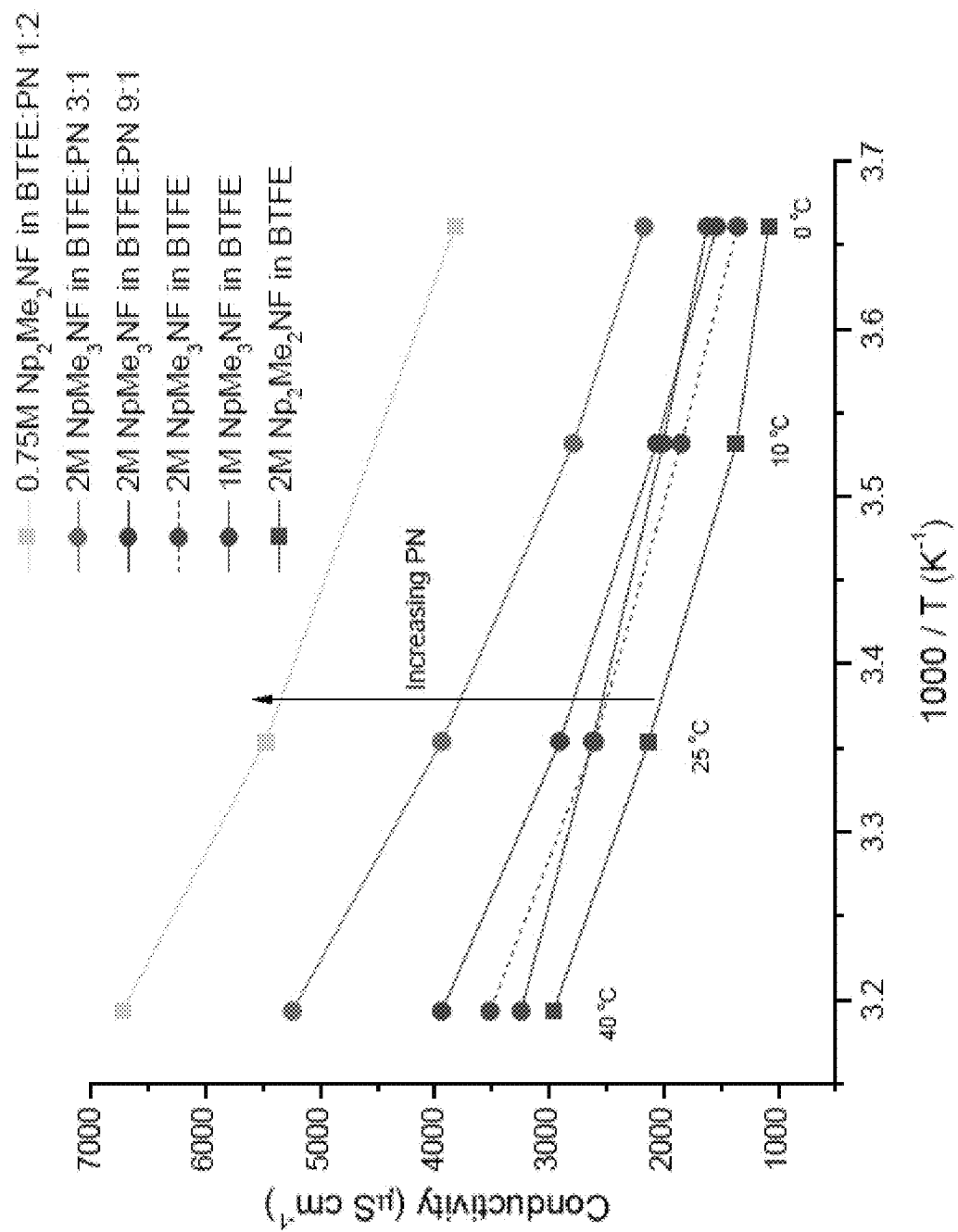
FIG. 15 is a plot of temperature-dependent ionic conductivity data for solutions of NpMe$_3$NF and Np$_2$Me$_2$NF in BTFE at various concentrations and PN content (by volume)

FIG. 15 illustrates temperature-dependent ionic conductivity data for solutions of $NpMe_3NF$ and $Np_2Me_2NF$ in BTFE at various concentrations and PN content (by volume). It is observed that the conductivities of 1.0 M and 2.0 M solutions of $NpMe_3NF$ in BTFE are very similar, indicating that $NpMe_3NF$ may not be fully dissociated into ions at these concentrations in BTFE. Temperature-dependent data for these two solutions follow slightly different curves (with a cross-over around 25° C.), indicating that a temperature-dependent dissociation equilibrium is operating in parallel with the expected change in conductivity with temperature due to ion kinetics.

A 2M solution of the more-substituted salt $Np_2Me_2NF$ in BTFE displayed even lower ionic conductivity, suggesting an even greater degree of ion-pairing, consistent with the calculations described above. Indeed, $Np_2Me_2NF$ is significantly less soluble in BTFE than $NpMe_3NF$, and it takes some time for dissolution to make a 2.0M solution of $Np_2Me_2NF$ in BTFE. In contrast, $NpMe_3NF$ dissolves at this (and higher) concentrations readily.

In general, addition of increasing amounts of PN is also observed to increase the conductivity significantly at nearly all temperatures, suggesting that this solvent type helps with ion dissociation by solvating both cation and anion. However, $Np_2Me_2NF$ is observed to be more soluble in PN than $NpMe_3NF$, in contrast to BTFE. Hence the more-substituted salt may be more useful in such mixed solvent systems where the concentration of BTFE is relatively low (e.g., <50 vol. %).

Figure 16A:
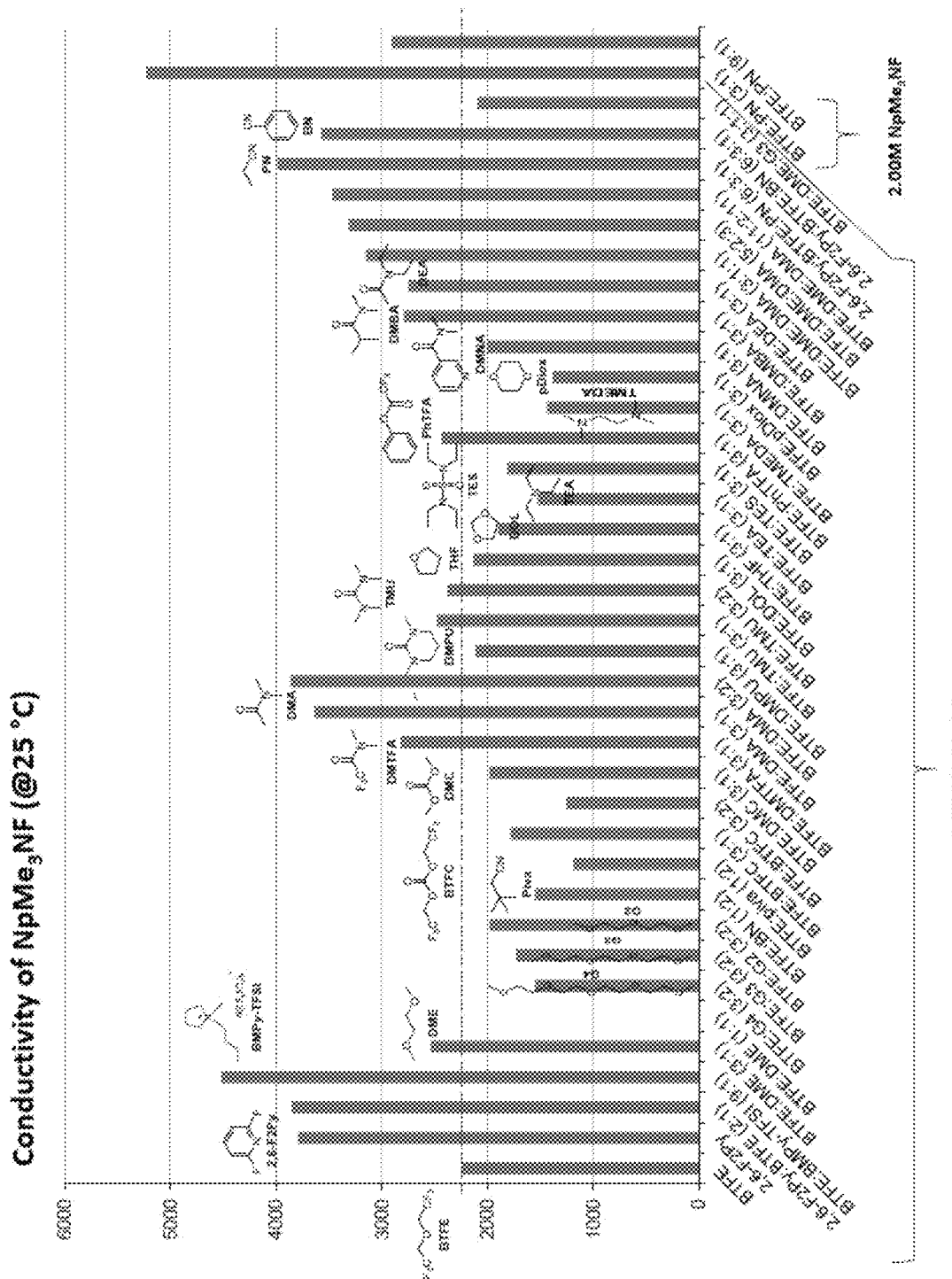
FIGS. 16A-16B are a bar graph of conductivity of solutions containing fluoride salts and non-aqueous solvent mixtures; (A) NpMe$_3$NF salt; (B) Np$_2$Me$_2$NF salt.
Figure 16B:
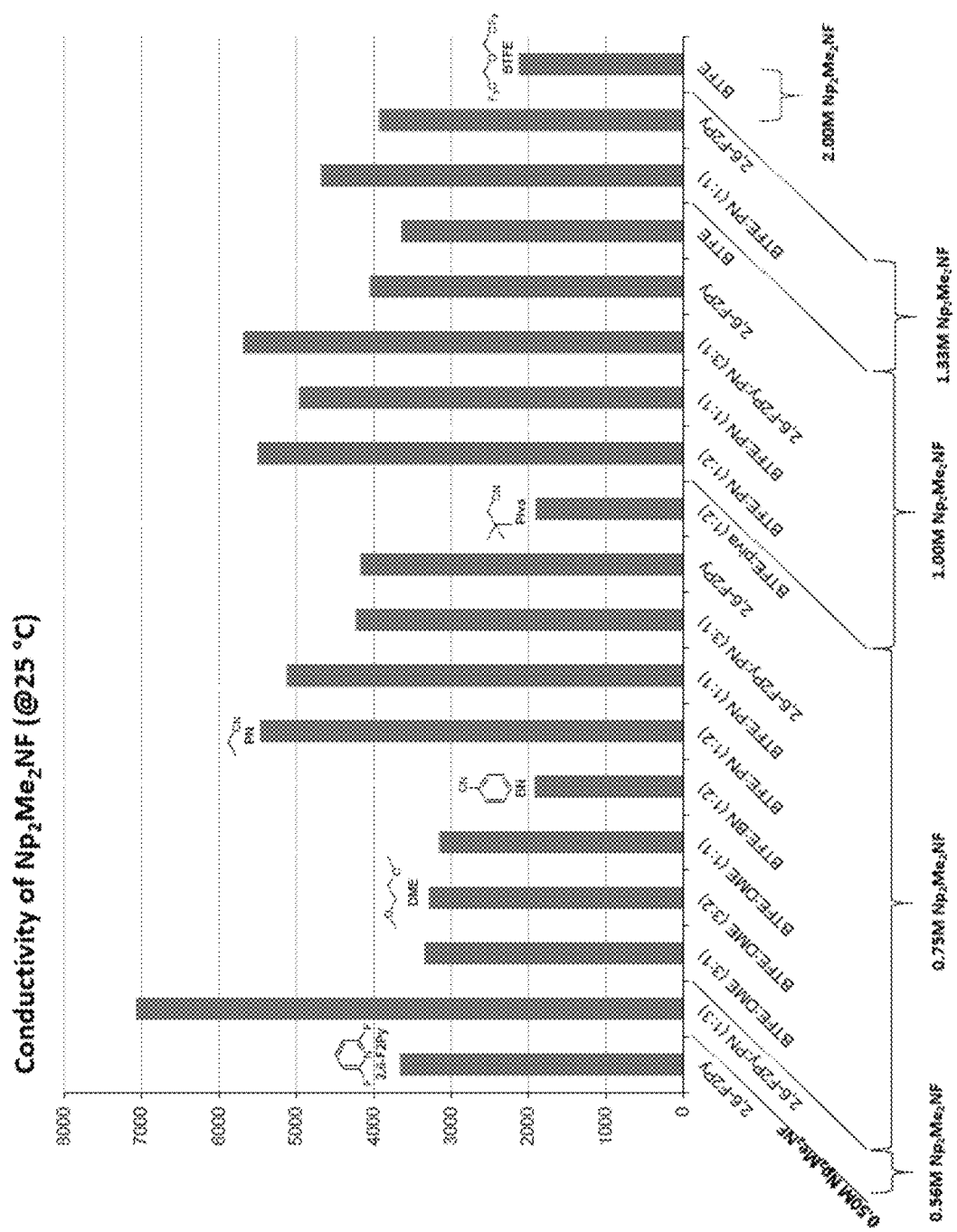

Further characterization of solvent mixtures is performed using $NpMe_3NF$ and $Np_2Me_2NF$ salts. FIG. 16A illustrates measured conductivities for mixtures of solvents and $NpMe_3NF$, while FIG. 16B illustrates measured conductivities for mixtures of solvents and $Np_2Me_2NF$. With regards to the $NpMe_3NF$ solutions, in certain cases, the conductivity may be increased from that observed for a BTFE mixture of salt at a given concentration through use of a solvent mixture. In particular, glymes (e.g., dimethoxyethane) and amides may be useful co-solvents to achieve such an effect. With regards to the $Np_2Me_2NF$ solutions, in certain cases, higher conductivity values can be measured compared to that for $NpMe_3NF$ mixtures due to the higher solubility of the $Np_2Me_2NF$ salt in certain solvents and mixtures.

(iii) Voltage Windows of $NpMe_3NF$ Solutions

Figure 17:
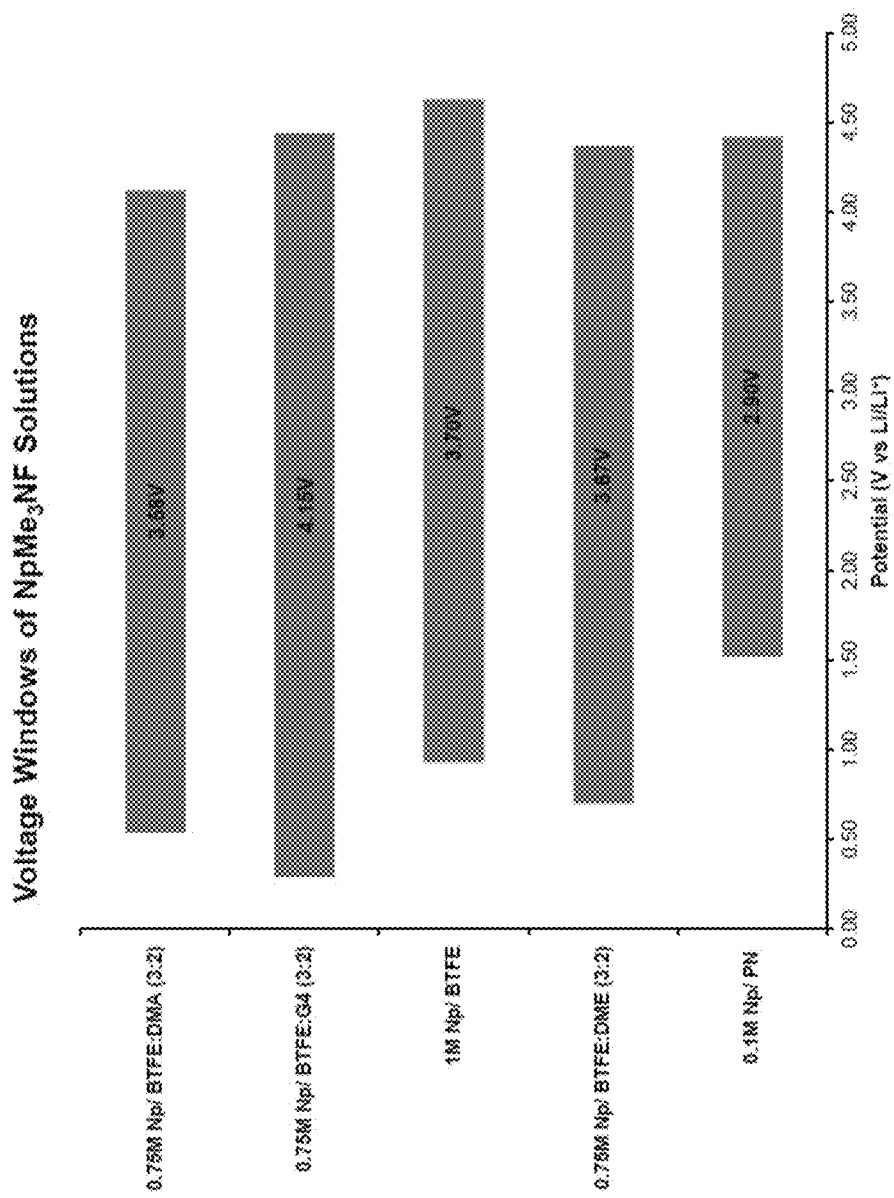
FIG. 17 is a bar graph of voltage windows measured from linear sweep voltammograms for embodiments of electrolyte solutions of the present disclosure.

Solutions of $NpMe_3NF$ in PN and BTFE are also investigated by linear sweep voltammetry to determine their voltage window. A Pt working electrode, Pt auxiliary and non-aqueous $Ag^+/Ag$ (MeCN) reference electrode, with Ar purge are employed for. The voltage windows for a limiting current of 100 $\mu A/cm^2$ are measured at 1 mV/s for electrolyte solutions of 0.75M $NpMe_3NF/BTFE:DMA$ (3:2), 0.75M $NpMe_3NF/BTFE:G4$ (3:2), 1M $NpMe_3NF/BTFE$, 0.75M $NpMe_3NF/BTFE:DME$ (3:2), and 0.1M $NpMe_3NF/PN$ illustrated in FIG. 17. The voltage window data suggests that these non-aqueous electrolyte solutions may possess a useful electrochemical window of at least 3V. Combined with their high conductivity, these non-aqueous solutions of fluoride salts may be employed as electrolytes for electrochemical applications such as fluoride-ion batteries, electrochemical double-layer capacitors and in electrochemical fluorination reactions.

Example 5—Electrochemical Tests of Positive Electrode

Electrochemical tests of Cu positive electrodes are further performed to compare the performance of embodiments of the disclosed electrolyte solutions within an electrochemical cell. Electrolyte solutions of $PN/NpMe_3NF$ and $BTFE/NpMe_3NF$ are examined. A standard three electrode electrochemical cell is utilized including a copper (II) fluoride working electrode, a platinum counter electrode, and an $Ag/Ag^+$ reference electrode. In operation, the charge and discharge reactions occurring within the cell are given by Equations (5) and (6) below:

$$\text{Disharge:} CuF_2 \rightarrow Cu \quad (5)$$

$$\text{Charge:} Cu \rightarrow CuF, CuF_2(Cu^{2+}) \quad (6)$$

During discharge, the constant current discharge is −50 $\mu A$ until −2.4 V and then constant voltage until current dropped to −5.0 $\mu A$. The constant current charge is 50 $\mu A$ until −0.3 V. Corresponding electrode X-ray diffraction (XRD) patterns for the initial state of the electrochemical cell, as well as after discharge and/or charge are further acquired.

Figure 18A:
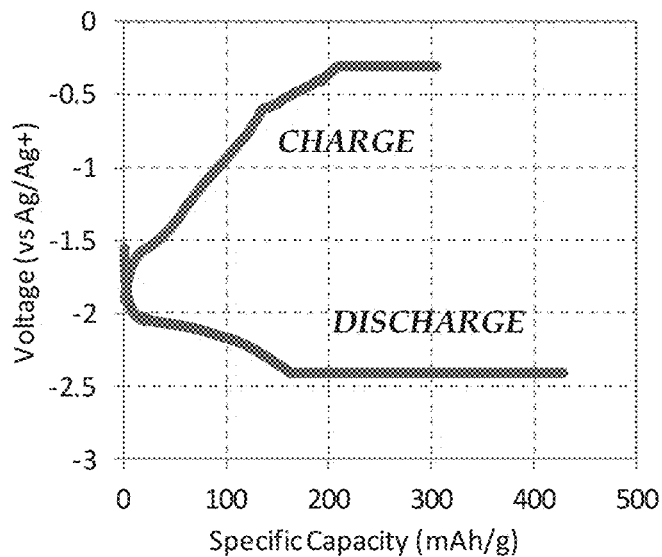
FIG. 18A is a plot of voltage as a function of specific capacity for electrochemical tests of an electrochemical cell including a Cu positive electrode and a NpMe$_3$NF/PN electrolyte solution.
Figure 18B:
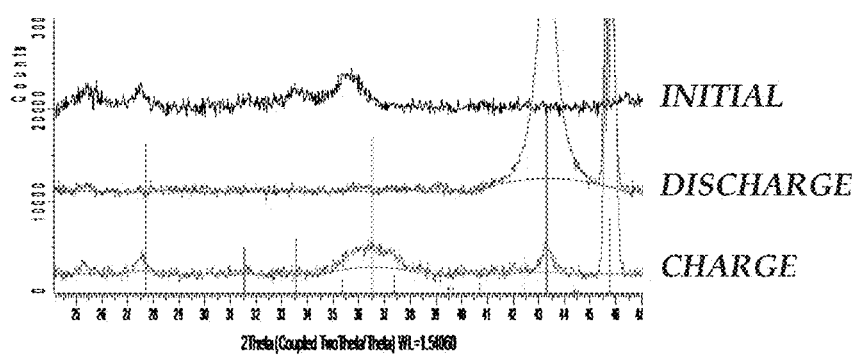
FIG. 18B is an X-ray diffraction spectrum of the Cu positive electrode of the electrochemical cell of FIG. 18A, measured under initial conditions, after discharge, and after charge.
Figure 18C:
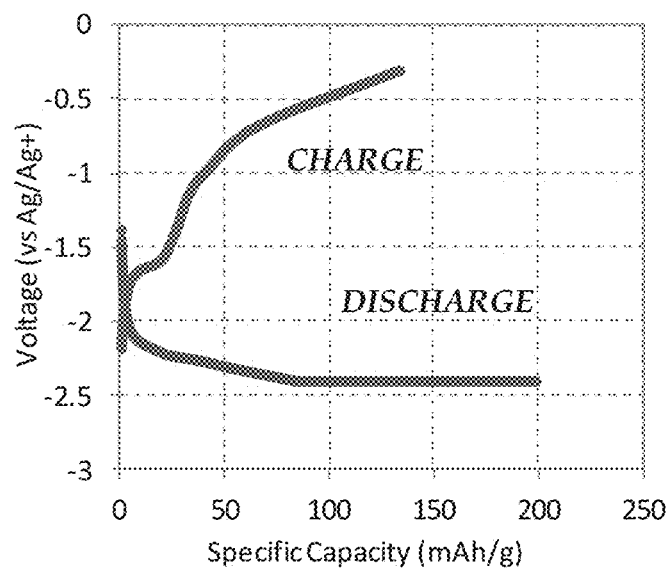
FIG. 18C is a plot of voltage as a function of specific capacity for electrochemical tests of an electrochemical cell including a Cu positive electrode and a NpMe$_3$NF/BTFE electrolyte solution.
Figure 18D:
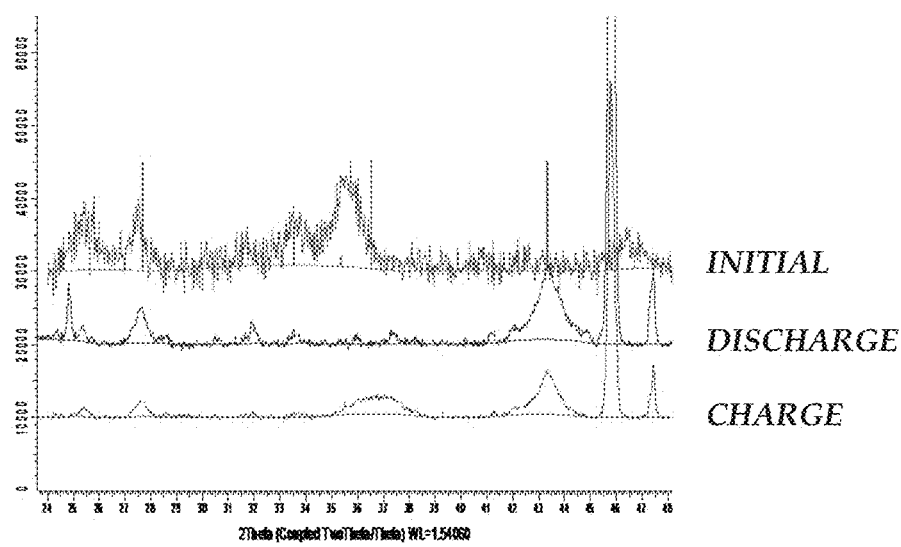
FIG. 18D is an X-ray diffraction spectrum of the Cu positive electrode of the electrochemical cell of FIG. 18C, measured under initial conditions and after discharge.

Voltage as a function of specific capacity for electrolyte solutions of $NpMe_3NF/PN$ and $NpMe_3NF/BTFE$ is presented in FIGS. 18A and 18C, respectively. It may be observed that the specific capacity of the cell containing the $NpMe_3NF/PN$ electrolyte solution is 428 mAh/g after discharge and 304 mAh/g after charge. The specific capacity of the cell containing the $NpMe_3NF/BTFE$ electrolyte solution is 198 mAh/g after discharge and 133 mAh/g after charge.

Notably, the capacity observed in electrochemical cells employing the $NpMe_3NF/PN$ electrolyte solution, 428 mAh/g, is approximately 81% of the theoretical capacity of $CuF_2$ (528 mAh/g). Furthermore, this capacity is significantly larger than that achieved from a conventional Li-ion battery system, lithium cobalt oxide, about 150 mAh/g.

Without being bound by theory, it is believed that the observed capacity and behavioral differences between the electrolyte solutions of $NpMe_3NF/PN$ and $NpMe_3NF/BTFE$ are due to interfacial resistance arising out of the different solvent mixtures. Resistance of electron transfer from $NpMe_3NF/PN$ into active material is considered to be low. Because of low resistance, higher capacity and discharge voltage is observed in $NpMe_3NF/PN$ as compared to $NpMe_3NF/BTFE$.

Corresponding electrode X-ray diffraction (XRD) spectra measured at the initial state of the electrochemical cell and after discharge and charge are illustrated in FIGS. 18B ($NpMe_2NF/PN$) and 18D ($NpMe_3NF/BTFE$). In each case, the XRD spectra measured after discharge clearly show the emergence of a peak corresponding to Cu and the disappearance of the peaks corresponding to CuF, $CuF_2$, reflecting the reduction of $Cu^{2+}$ to Cu, as compared to the initial state, in accordance with Equation (5). Furthermore, the XRD spectra measured after charge exhibits the reemergence of the peak corresponding to $CuF_2$ and reduction of the peak corresponding to Cu, reflecting the oxidation of Cu to $Cu^-$ and $Cu^{2+}$, in accordance with Equation (6).

These voltage and XRD measurements demonstrate that $CuF_2$ can be electrochemically reduced and re-fluorinated in these electrolyte systems and that reduction activity is solvent dependent. Furthermore, PN may have an effect to facilitate electron transfer.

Statements Regarding Chemical Compounds and Nomenclature

As used herein, the term "group" may refer to a functional group of a chemical compound. Groups of the present compounds refer to an atom or a collection of atoms that are a part of the compound. Groups of the present compounds may be attached to other atoms of the compound via one or more covalent bonds. Groups may also be characterized with respect to their valence state. The present compounds includes groups characterized as monovalent, divalent, trivalent, etc. valence states.

As used herein, the term "substituted" refers to a compound where a hydrogen is replaced by another functional group.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups where the alky portion of the groups is substituted as provided herein in connection with the description of alkyl groups. As used herein MeO— refers to $CH_3O—$.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those that are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6-, 7- or 8-member aromatic rings, including heterocyclic aromatic rings. The term heteroaryl specifically refers to aryl groups having at least one 5-, 6-, 7- or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein provided in a covalently bonded configuration in the compounds of the disclosure at any suitable point of attachment. In embodiments, aryl groups contain between 5 and 30 carbon atoms. In embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups where the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups where the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As used herein, the terms "alkylene" and "alkylene group" are used synonymously and refer to a divalent group derived from an alkyl group as defined herein. The present disclosure may include compounds having one or more alkylene groups. Alkylene groups in some compounds function as attaching and/or spacer groups. Compounds of the present disclosure may have substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The present disclosure may include compounds having one or more cycloalkylene groups. Cycloalkyl groups in some compounds function as attaching and/or spacer groups. Compounds of the present disclosure may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The present disclosure may include compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Non-limiting examples include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein. The present disclosure may include compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Non-limiting examples include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The present disclosure may include compounds having one or more alkenylene groups. Alkenylene groups in some compounds function as attaching and/or spacer groups. Non-limiting examples include substituted and/or unsubstituted $C_2$-$C_{20}$ alkenylene, $C_2$-$C_{10}$ alkenylene and $C_2$-$C_5$ alkenylene groups.

As used herein, the terms "cylcoalkenylene" and "cylcoalkenylene group" are used synonymously and refer to a divalent group derived from a cylcoalkenyl group as defined herein. The present disclosure may include compounds having one or more cylcoalkenylene groups. Cycloalkenylene groups in some compounds function as attaching and/or spacer groups. Non-limiting examples include substituted and/or unsubstituted $C_3$-$C_{20}$ cylcoalkenylene, $C_3$-$C_{10}$ cylcoalkenylene and $C_3$-$C_5$ cylcoalkenylene groups.

As used herein, the terms "alkynylene" and "alkynylene group" are used synonymously and refer to a divalent group derived from an alkynyl group as defined herein. The present disclosure may include compounds having one or more alkynylene groups. Alkynylene groups in some compounds function as attaching and/or spacer groups. Non-limiting examples include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy where n is an integer from 1 to 10, preferably 1 to 4, and more preferably for some embodiments 1 to 3.

As to any of the groups described herein that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds. Optional substitution of alkyl groups includes substitution with one or more alkenyl groups, aryl groups or both, where the alkenyl groups or aryl groups are optionally substituted. Optional substitution of alkenyl groups includes substitution with one or more alkyl groups, aryl groups, or both, where the alkyl groups or aryl groups are optionally substituted. Optional substitution of aryl groups includes substitution of the aryl ring with one or more alkyl groups, alkenyl groups, or both, where the alkyl groups or alkenyl groups are optionally substituted.

Optional substituents for any alkyl, alkenyl and aryl group includes substitution with one or more of the following substituents, among others: halogen, including fluorine, chlorine, bromine or iodine; pseudohalides, including —CN;

—COOR, where R is a hydrogen or an alkyl group or an aryl group and more specifically where R is a methyl, ethyl, propyl, butyl, or phenyl group all of which groups are optionally substituted;

—COR, where R is a hydrogen or an alkyl group or an aryl group and more specifically where R is a methyl, ethyl, propyl, butyl, or phenyl group all of which groups are optionally substituted;

—CON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$, where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring that can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR, where R is an alkyl group or an aryl group and more specifically where R is a methyl, ethyl, propyl, butyl, or phenyl group, all of which are optionally substituted;

—OCOOR, where R is an alkyl group or an aryl group;

—SO$_2$N(R)$_2$, where each R, independently of each other R, is a hydrogen, or an alkyl group, or an aryl group all of which are optionally substituted and where R and R can form a ring that can contain one or more double bonds and can contain one or more additional carbon atoms;

—OR, where R is H, an alkyl group, an aryl group, or an acyl group all of which are optionally substituted. In a particular example R can be an acyl yielding —OCOR", where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds.

Statements Regarding Incorporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (where XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An electrochemical cell, comprising:
   a positive electrode;
   a negative electrode; and
   an electrolyte solution provided between said positive electrode and said negative electrode, said electrolyte solution comprising:
   a first fluoride salt, comprising:
     one or more first fluoride ions; and
     a first organic cation, wherein:
     the first organic cation does not possess a carbon in the β-position having a bound hydrogen;
     the cation charge center of the first organic cation is N, P, S, or O; and
     the first fluoride salt is a substituted or unsubstituted (2,2-dimethylpropyl)trimethylammonium fluoride (NpMe$_3$NF) or a substituted or unsubstituted bis(2,2-dimethylpropyl)dimethylammonium fluoride (Np$_2$Me$_2$NF);
   a second fluoride salt that is different than the first fluoride salt, the second fluoride salt comprising:
     one or more second fluoride ions; and
     a second organic cation, wherein
     the cation charge center of the second organic cation is N, P, S, or O; and
   one or more non-aqueous solvents, at least one of the one or more non-aqueous solvents being fluorinated and comprising at least one functional group characterized by the form [X—(CH$_2$)$_n$—Y], where X and Y are polar functional groups having a combined effect to confer a partial positive charge on the CH$_2$ group or groups and n=1 or 2;
   wherein said fluoride salt is provided to said one or more non-aqueous solvents in an anhydrous form; and
   wherein the total concentration of said first and said second fluoride ions dissolved in said electrolyte solution is selected from the range of 0.5 M to 20 M.

2. The electrochemical cell of claim 1, wherein the total concentration of said first and said second fluoride ions dissolved in said electrolyte solution is greater than or equal to 1 M and less than or equal to 20 M.

3. The electrochemical cell of claim 1, wherein Y is O or S and X is a functional group selected from the group consisting of ethers, esters, acid anhydrides, amines, amides, carbonates, sulfones, sulfonyl esters, phosphites, phosphates, nitriles, nitro, aldehydes, acetates, SF$_5$, or fluorocarbons.

4. The electrochemical cell of claim 1, wherein the at least one of the one or more non-aqueous solvents is characterized by the formula (FX7a) (FX7b), (FX7c), (FX7d), (FX7e), or (FX7g):

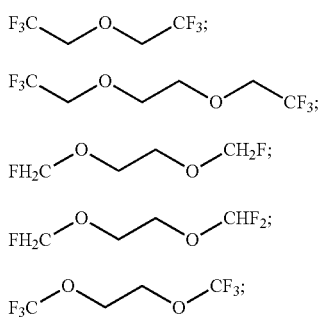

(FX7a)
(FX7b)
(FX7c)
(FX7d)
(FX7e)

or

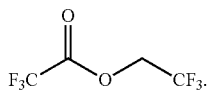

(FX7g)

5. The electrochemical cell of claim 1, wherein the at least one of the one or more non-aqueous solvents is a fluorinated phosphite or any combination thereof and the fluorinated phosphite is characterized by the formula (FX8a):

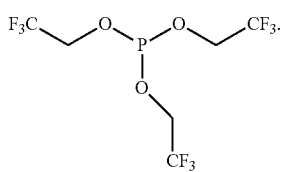

(FX8a)

6. The electrochemical cell of claim 1, wherein the at least one of the one or more non-aqueous solvents is a fluorinated ester or anhydride or any combination thereof and the fluorinated ester or anhydride is characterized by the formula (FX9b):

(FX9b)

7. The electrochemical cell of claim 1, wherein the at least one of the one or more non-aqueous solvents is a nitrile or any combination thereof and the nitrile is characterized by the formula (FX10c):

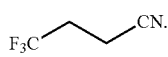

(FX10c)

8. The electrochemical cell of claim 1, wherein the at least one of the one or more non-aqueous solvents is characterized by the formula (FX12a):

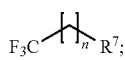

(FX12a)

wherein $R^7$ is a halo group or a halogen-substituted $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_{20}$ alkyl, $C_2$-$C_{20}$ alkoxycarbonyl, $C_4$-$C_{30}$ aliphatic, $C_4$-$C_{30}$ cycloaliphatic, or $C_4$-$C_{30}$ aromatic; and wherein n is an integer selected from the range of 1 to 20.

9. The electrochemical cell of claim 1, wherein the electrolyte solution provides an ionic conductivity greater than or equal to 0.1 mS/cm at 25° C.

10. The electrochemical cell of claim 1, wherein the one or more non-aqueous solvents comprises a second non-aqueous solvent being an ether or a glyme.

11. The electrochemical cell of claim 1, wherein the at least one of the one or more non-aqueous solvents is selected from the group consisting of bis(2,2,2-trifluoroethyl)ether (BTFE), tris(2,2,2-trifluoroethyl)phosphite (TTFP), 2,2,2-trifluoroethyl trifluoroacetate (TFE-TFA), methoxyacetonitrile (MeOAN), 3-methoxypropionitrile (3-MeOPN), and fluoroethylene carbonate (FEC).

* * * * *